United States Patent
Raines et al.

(10) Patent No.: US 10,577,303 B1
(45) Date of Patent: Mar. 3, 2020

(54) REAGENTS AND METHODS FOR ESTERIFICATION

(71) Applicant: Wisconsin Alumni Research Foundation, Madison, WI (US)

(72) Inventors: Ronald T. Raines, Madison, WI (US); Nicholas Adam McGrath, Fairmont, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/212,381

(22) Filed: Mar. 14, 2014

Related U.S. Application Data

(60) Provisional application No. 61/783,385, filed on Mar. 14, 2013.

(51) Int. Cl.
*C07C 67/18* (2006.01)
*C07C 245/12* (2006.01)

(52) U.S. Cl.
CPC ............ *C07C 67/18* (2013.01); *C07C 245/12* (2013.01)

(58) Field of Classification Search
CPC .............................. C07C 67/18; C07C 245/12
See application file for complete search history.

(56) References Cited

U.S. PATENT DOCUMENTS

| | | |
|---|---|---|
| 8,350,014 B2 | 1/2013 | Raines et al. |
| 8,871,916 B2 | 10/2014 | Raines et al. |
| 2016/0067342 A1 | 3/2016 | Raines et al. |

OTHER PUBLICATIONS

Froussios et al. "Nouvelle methode de protection du carboxyle des acides a-amines: esters 9-fluorenyliques" Tetrahedron Letters, 1989, vol. 30, pp. 3413-3414.*
Ballard, "Small Molecule Control of Biological Function", 2008, p. 18.*
Bräse et al. (2005) "Organic azides: an exploding diversity of a unique class of compounds," *Angew. Chem. Int. Ed.* 44:5188-5240.
Chibnall et al. (1958) "Studies on the amide and C-terminal residues in proteins. 3. The esterification of proteins," *Biochem. J.* 68:114-118.
De et al. (2009) "Solvent-Promoted and -Controlled Aza-Michael Reaction with Aromatic Amines," *J. Org. Chem.* 74:6260-6265.
Delpierre et al. (1965) "Inactivation of pepsin by diphenyldiazomethane," *Proc. Natl. Acad. Sci. USA*. 54:1161-1167.
Doscher et al. (1961) "Chemical derivatives of alpha-chymotrypsinogen IV. A comparison of the reactions of alpha-chymotrypsinogen and of simple carboxylic acids with diazoacetamidem," *J. Biol. Chem.* 236:1328-1337.
Doyle (1986) "Catalytic methods for metal carbene transformations," *Chem. Rev.* 86:919-939.
Dumitrescu et al. (Jan. 19, 2011) "Nonmetal Catalyzed Insertion Reactions of Diazocarbonyls to Acid Derivatives in Fluorinated Alcohols," *Org. Lett.* 13:692-695.

Furrow et al. (2004) "A general procedure for the esterification of carboxylic acids with diazoalkanes generated in situ by the oxidation of N-tert-butyldimethylsilylhydrazones with (difluoroiodo)benzene," *J. Am. Chem. Soc.* 126:12222-12223.
Grossberg et al. (1960) "Nature of the Combining Site of Antibody against a Hapten Bearing a Positive Charge," *J. Am. Chem. Soc.* 82:5478-5482.
Jewett et al. (2010) "Rapid Cu-Free Click Chemistry with Readily Synthesized Biarylazacyclooctynones," *J. Am. Chem. Soc.* 132:3688-3690.
Larson et al. (1981) "Stabilization of charged substrates by first- and second-row heteroatoms," *J. Am. Chem. Soc.* 103:410-416.
Matthews et al. (1975) "Equilibrium acidities of carbon acids. VI. Establishment of an absolute scale of acidities in dimethyl sulfoxide solution," *J. Am. Chem. Soc.* 97:7006-7014.
McGarrity et al. (1980) "Hydrolysis of diazomethane-kinetics and mechanism," *J. Am. Chem. Soc.* 102:7303-7308.
McGrath et al. (Aug. 2, 2012) "Diazo compounds as highly tunable reactants in 1,3-dipolar cycloaddition reactions with cycloalkynes," *Chem. Sci.* 3:3237-3240.
Myers et al. (2009) "A phosphine-mediated conversion of azides into diazo compounds," *Angew. Chem. Int. Ed.* 48:2359-2363.
Riehm et al. (1965) "Structural Studies of Ribonuclease. XVII. A Reactive Carboxyl Group in Ribonuclease," *Biochemistry*. 4:772-782.
Szele et al. (1983) "Reactions of Alkenediazonium Salts. Part 1. 2,2-Diethoxyethene-diazonium hexachloroantimonate: A diazonium, a carbenium or an oxonium salt?" *Helv. Chim. Acta.* 66:1691-1703.
Taft et al. (1988) "Structural and solvent effects evaluated from acidities measured in dimethyl sulfoxide and in the gas phase," *Acc. Chem. Res.* 21:463-469.

(Continued)

*Primary Examiner* — Joseph R Kosack
(74) *Attorney, Agent, or Firm* — Leydig, Voit & Mayer, Ltd.

(57) ABSTRACT

A method for esterification of one or more carboxylic acid groups in a compound containing one or more carboxylic acid groups wherein the esterification reagent is a diazo-compound of formula:

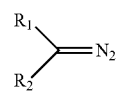

wherein the $R_1$ and $R_2$ groups of the diazo compound are selected such that the corresponding organic compound of formula:

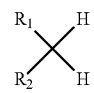

exhibits a —C—H pKa value between 18 and 29 as measured in DMSO. Specific reagents and methods for esterification are provided. The esterification reagents provided exhibit high selectivity for esterification of carboxylic acid groups over reaction with amine, alcohol or thiol groups in the compound containing one or more carboxylic acid groups. The method can be used to selectively esterify carboxylic acid groups in peptides or proteins.

25 Claims, No Drawings

(56) References Cited

OTHER PUBLICATIONS

Tian et al. (Mar. 12, 2012) "Selective esterase-ester pair for targeting small molecules with cellular specificity," *Proc. Natl. Acad. Sci. USA.* 109:4756-4761.
Ye et al. (1994) "Organic Synthesis with α-Diazo Carbonyl Compounds," *Chem. Rev.* 94:1091-1160.
Froussios et al. (1989) "Novelle Methode De Protection Du Carboxyle Des Acid a-Amine: Esters 9-Fluorenyliques," Tetrahedron Letts, 30(26):3413-3414 full reference with English translation.
McGrath N.A. et al. (2015) "Diazo compounds for the bioreversible esterification of proteins," Chemical Science 6:752-755.
Bordwell, F. G., "Equilibrium acidities in dimethyl sulfoxide solution," Acc. Chem. Res. 21:456-463, 1988.
Aboderin A. A. et al. (1965) "Benzhydryl Esters of Amino Acids in Peptide Synthesis," J. Am. Chem. Soc. 87(23): 5469-5472.
Aboderin A. A et al. (1966) "Inactivation of Chymotrypsin by Diphenyldiazomethane," Proc. Nat. Acad. Sci. (USA) 56:1252-1259.
Bayliss R. S. et al. (1969)"An Aspartic Acid Residue at the Active Site of Pepsin," Biochem. J. 113:377-386.
Chang, J.A. and Kresge, A.J. (2003) "Kinetics and mechanism of acid-catalyzed hydrolysis of the diazo functional group of diazophenylacetamide," J. Phys. Org. Chem. 16(9):598-602.
Delpierre, G.R. et al. (1966) "Specific Inactivation Of Pepsin By A Diazo Ketone," Proc. Nat. Acad. Sci. 56: 1817-1822.
Hamilton G.A. et al. (1967) "The inactivation of pepsin by an equimolar amount of I-diazo-4-phenylbutanone 2," Biochem. Biophys. Res. Comm. 26(2):1967.
Husain S.S. et al. (1971) Bifunctional Inhibitors of pepsin, Proc. Nat. Acad. Sci. USA 68(11):2765-2768.
Jarowicki K. and Kocienski P. (2000) "Protecting Groups," J. Chem. Soc., Perkin Trans. 1, 2000, 2495-2527.
Josa-Cullere et al. (Oct. 14, 2014) "Diazo group as a new chemical reporter for bioorthogonal labelling of biomolecules," RSC Adv. 4:52241-52244 (Royal Society of Chemistry).
Lavis L.D. (2008) "Ester Bonds in Prodrugs," ACS Chemical Biol. 3(4):203-206.
McGrath N.A. et al. (Aug. 2, 2012) "Diazo compounds as highly tunable reactants in 1,3-dipolar cycloaddition reactions with cycloalkynes," Chem. Sci. 3:3237-3240.
Mix K.A. and Raines, R.T. (May 4, 2015) "Optimized Diazo Scaffold for Protein Esterification," Organic Letts. 17:2358-2361.
Mix, K.A. et al. (Oct. 2016) "Diazo Compounds: Versatile Tools for Chemical Biology," ACS Chemical Biology DOI: 10.1021/acschembio.6b00810.
More O'Ferrall R.A. M. et al. (1964) "Medium Effects, Isotope Rate Factors, and the Mechanism of the Reaction of Diphenyldiazomethane with Carboxylic Acids in the Solvents Ethanol and Toluene," J. Am. Chem. Soc. 86(24):5553-5561.
Roberts , J.D. (1950)"The Kinetics and Mechanism of the Acid-Catalyzed Reaction of Diphenyldiazomethane with Ethyl Alcohol," J. Amer. Chem. Soc. 72:4869-4879.
Roberts J.D. et al. (1951) "The Kinetics and Mechanism of the Reaction of Diphenyldiazomethane and Benzoic Acid in Ethanol," J. Amer. Chem. Soc. 73: 760-765.
Sammakia, T. (2001) Diphenyldiazomethane, Encyclopedia of reagents for Organic Synthesis, John Wiley & Sons, Ltd https://doi.org/10.1002/047084289X.rd413.

* cited by examiner

REAGENTS AND METHODS FOR ESTERIFICATION

CROSS-REFERENCE TO RELATED APPLICATIONS

This application claims the benefit of U.S. provisional application 61/783,385, filed Mar. 14, 2013, which is incorporated by reference herein in its entirety.

STATEMENT REGARDING GOVERNMENT SUPPORT

This invention was made with government support under GM096712 and GM044783 awarded by the National Institutes of Health. The government has certain rights in the invention.

BACKGROUND OF THE INVENTION

Chemoselective transformations [1-3] are of key importance in modern chemical biology. Proteins, peptides and amino acids have carboxyl groups in side groups and at the C-terminus. Methods and reagents for selective esterification of such carboxyl groups, particularly those in polypeptides and proteins, which are efficient and give high yield and which can be carried out in buffered aqueous solution are of particular interest. Esterification reactions that do not require a catalyst are also of particular interest.

It is also of interest for certain applications that the esters formed are "bio-reversible" such that the ester groups are removable by esterases. In a specific application, esterification can be employed to functionalize a protein with moieties that direct the protein towards a particular cell type or and/or which facilitate its cellular uptake. If esterification is bio-reversible, the groups added to target the protein to a cell or to enhance its uptake into the cell can be removed by endogenous enzymes in the cell to regenerate native protein.

It has recently been reported that diazo-compounds can be employed in place of azides as the 1,3-dipole in 1,3-dipolar cycloaddition reactions with alkynes.[4] The use of diazo-compounds in such reactions was at least in part made feasible with the availability of methods that convert azides into diazo-compounds using a phosphinoester. [5] These methods are described in U.S. Pat. No. 8,350,014 which is incorporated by reference herein in its entirety for its description of such methods and diazo-compounds prepared by the methods.

The esterification of carboxylic acids with diazomethane has biological potential, but suffers from non-specific reactivity with the hydroxyl groups on lysine and tyrosine side chains.[6] In addition, this process only provides access to methyl esters, which are not particularly useful in biologic systems due to their non-specific lability toward various esterases present in biological milieu.[7] Compounds with targeted specificity for common biologic functional moieties that preclude deleterious side reactions are particularly useful.[8]

Stabilized diazo compounds have found widespread use in synthetic organic chemistry.[9] This is primarily due to their ability to react with carboxylic acids and amides by forming metal carbenoids [10] to facilitate OH- or NH-bond insertion respectively. [11,12] In an effort to avoid the use of toxic metals, it was recently reported that fluorous organic solvents [13] were sufficient to help facilitate the reaction due to their high polarity and poor nucleophilicity.[14] Additionally, various non-stabilized diazo compounds generated in-situ were shown to be capable of carrying out the esterification of carboxylic acids [15], but their unstable nature limits their biological utility.

Early use of stabilized diazo compounds in a biological context involved adding diazo glycinamide [16], diphenyldiazomethane [17] or diazoacetamide [18,19] to identify the reactive carboxylic acids on proteins. These methods all required adding a vast excess of the diazo compound and tedious monitoring of reaction pH to achieve modest labeling. However, new methods for the chemoselective generation of biological esters from carboxylic acids could be of significant interest for protein labeling (e.g., isotopic, radiolabeling, or fluorescent labeling) and to provide a way to controllably and efficiently increase protein lipophilicity and therefore promote cellular uptake.[20]

SUMMARY OF THE INVENTION

The invention provides methods and reagents for esterification of biological molecules including proteins, polypeptides and peptides. The invention employs certain diazo compounds of general formula I:

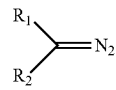

to convert carboxylic acid groups of biological molecules, particularly those of the side chains and C-terminus of proteins, polypeptides and peptides into esters. In specific embodiments, the esterification can be carried out in buffered aqueous solvent at pH ranging from 5-7 and preferably 5.5 to 6.5 and does not require the use of a catalyst.

More specifically, high yield esterification is provided when the diazo compound is one in which the organic compound to which the diazo group is formally attached, i.e., the corresponding compound:

exhibits a —C—H pKa value between 18 and 29 as measured in DMSO. [28] An organic diazo compound can, in a formal sense, be characterized as addition of nitrogen to an organic compound $R_1(R_2)CH_2$ with removal of two hydrogens:

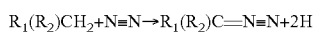

It has been found that selectivity and reactivity of an organodiazo compound for esterification of carboxylic acids in aqueous solution are correlated with the pKa of the C—H of this formal precursor organic compound $R_1(R_2)CH_2$.

Organodiazo compounds wherein this formal precursor has a pKa less than 18 as measured in DMSO are unreactive under the conditions of esterification herein. Organodiazo compounds wherein this formal precursor has a pKa greater than 29 as measured in DMSO are too reactive under the conditions of esterification herein, are not chemoselective for reaction with carboxylic acid groups and will react with functional groups other than carboxylic acids, e.g., hydroxyl groups, such as are found in serine, threonine and tyrosine side groups. Additionally, the organodiazo compounds of this invention were found to be unreactive, under the conditions employed in methods herein, with other common functional groups present in biological systems, e.g., amines, alcohols and thiols.

In a specific embodiment, the diazo-compounds useful in this invention have formula I $R_1$ is an electron withdrawing group. In another specific embodiment, the diazo-compounds useful in this invention have formula I, $R_1$ is an electron withdrawing group and $R_2$ is an organic group that contains an electron withdrawing group but wherein the electronic withdrawing group is separated from the >C=N$_2$ group by 3 or more carbon bonds.

In a specific embodiment, diazo-compounds useful in the invention are those of formula I where:

$R_1$ is hydrogen, or an optionally substituted alkyl, alkenyl, alkynyl, aryl, alkyl aryl, aryl alkyl, heteroaryl, or heterocyclic group and $R_2$ is an optionally substituted alkyl, alkenyl, alkynyl, aryl, alkyl aryl, aryl alkyl, heteroaryl, heterocyclic group, where $R_1$ and $R_2$ together optionally form a 5- to 10-member ring which may be an optionally substituted carbocyclic ring or an optionally substituted heterocyclic ring in which one or more of the ring atoms can be replaced with —CO—, —O—, —CS—, —S— or —NR—, where R is hydrogen or an alkyl having 1-3 carbon atoms. In a specific embodiment, at least one of $R_1$ or $R_2$ comprises an electron withdrawing group (EWG) or $R_1$ or $R_2$ together form a 5- to 10-member ring which comprises or is substituted with one or more EWG. In a specific embodiment, one or both of $R_1$ or $R_2$ are alkyl, alkenyl, alkynyl, aryl, alkyl aryl, aryl alkyl groups substituted with one or more EW groups. In an embodiment, one or both of $R_1$ or $R_2$ are alkyl, alkenyl, alkynyl, or aryl groups substituted with one or more EW groups. A number of EW groups are known in the art and include, among others, nitro, cyano, halogen, ammonium (—NR'$_3^+$), aryloxy, alkoxy, sulfonic ester (—SO$_2$—R'), sulfonium (—S(R')$_2^+$), phosphonium (—P(R')$_3^+$), —COOR', —COR', —CON(R')$_2$, —OCOR', alkylthio, arylthio, aryl, —C≡CR', and —C=CR'$_2$, where each R' independently, is hydrogen, or an optionally substituted alky, alkenyl, alkynyl, aryl, alkylaryl, or arylalkyl, where two R' on the same atom may together with that atom form a 5- to 8-member carbocyclic or heterocyclic ring in which one or more ring atoms can be replaced with —CO—, —O—, —CS—, —S— or —NR—, where R is hydrogen or an alkyl group having 1-3 carbon atoms.

In a specific embodiment, the organodiazo compounds useful in this invention are those that are prepared by methods as described in U.S. Pat. No. 8,350,014. The esters formed by this method, particularly those formed in proteins, polypeptides and peptides are found to be removable by esterases and as such esterification is bio-reversible.

The invention provides a method for esterifying one or more carboxylic acid groups in an organic or biological molecule which comprises contacting the organic or biological molecule with a diazo-compound of this invention. In a specific embodiment, the reaction is carried out in an aqueous solution. In a specific embodiment, the reaction is carried out in a water/organic solvent mixture. In specific embodiments, the organic solvent is acetonitrile, methanol, ethanol, THF or related ethers. In specific embodiments, the organic solvent is acetonitrile. In specific embodiments, the reaction is carried out in solvent containing up to 70% of buffer with organic solvent. In specific embodiments, the reaction is carried out in solvent containing from 10-70% (by volume) of buffer with organic solvent. In specific embodiments, the reaction is carried out in an organic solvent selected from acetonitrile, methanol, ethanol, THF or related ethers. The composition of the solvent is dependent upon the solubility of the diazo-compound in water. In a specific embodiment, dependent upon the solubility of the diazo-compound, the reaction is carried out in buffered aqueous solution. In a specific embodiment, the reaction is carried out at a pH ranging from 5 to 7 and more preferably 5.5 to 6.5. In a specific embodiment, the reaction is carried out at a temperature ranging from about room temperature to about 40° C. In a specific embodiment, the reaction is carried out at ambient temperature. In a specific embodiment, the reaction is carried out at a temperature ranging from 30-37° C. In a specific embodiment, the reaction is carried out at a temperature ranging from 25-30° C.

Additional aspects and embodiments of the invention will become apparent to one of ordinary skill in the art on review of the following detailed description and non-limiting examples.

DETAILED DESCRIPTION OF THE INVENTION

This invention is based at least in part on studies of the reactivity of diazo-compounds for esterification of carboxylic acid groups as a function of their structure and electronic properties. In initial experiments, reactivity of diazofluorene was compared with that of diazobenzylacetamide. Regardless of steric hindrance or pKa of the carboxylic acid, higher yields and faster reaction times were observed for diazofluorene than for diazoacetamide in acetonitrile. (Example 1, Scheme 1) In aqueous solvent, diazobenzylacetamide largely reacted with water to form the corresponding alcohol. In contrast, diazofluorene showed efficient reactivity even in the presence of the competing nucleophile, water. (Example 2, Scheme 2). The diazofluorene generally exhibited better chemoselectivity with carboxylic acid groups compared to other groups, particularly alcohols. The diazofluorene further exhibited more efficient and more highly selective esterification of a representative protein RNase A.

As a result of a survey of reactivity of diazo-compounds, it has been found that selectivity and reactivity of an organodiazo compound of formula:

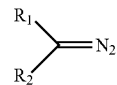

for esterification of carboxylic acids in aqueous solution are correlated with the pKa of the C—H of the corresponding organic compound $R_1(R_2)CH_2$ in DMSO. [28-35] Thus, diazo-compound useful in the invention can be selected based on a measurement of the pKa of such corresponding non-diazo compounds in DMSO. It is noted that the pKa's of a large number of organic compounds as measured in DMSO have been reported. [28-35] The pKa's of additional organic compounds can be measured in DMSO employing the methods described in the art. [28-35] Data already acquired by measurement of pKa's in DMSO that is publicly available in the literature [See, for example, www.chem.wisc.edu/areas/reich/pkatable/] can in addition be used to estimate the pKa's of structurally analogous compounds for which data is not yet available.

Additional diazo-compounds which exhibit high efficiency and high selectivity esterification, particularly in aqueous solutions include compounds of formulas II or III or IIIA:

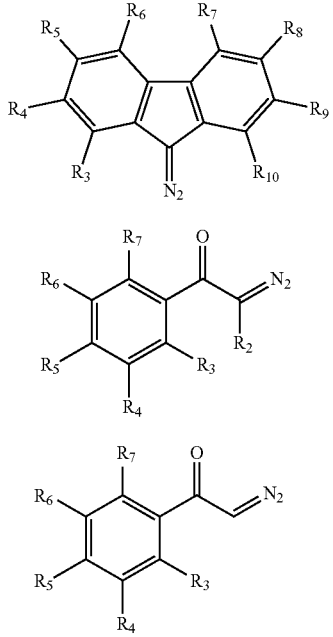

where:

R$_2$ is selected from hydrogen, alkyl, alkenyl, alkynyl, alkoxy, aryl, aryloxy, carbocyclic, carbocyclyloxy, heteroaryl, heteroaryloxy, heterocyclyl, or heterocyclyloxy, each of which groups is optionally substituted;

R$_3$-R$_{10}$ are selected from hydrogen, alkyl, alkoxy, alkenyl, alkenoxy, alkynyl, alkynoxy, aryl, aryl oxy, alkylaryl, alkylaryloxy, arylalkyl, arylalkyloxy, heteroaryl, heteroaryloxy, carbocyclic, carbocyclyloxy, heterocyclic or heterocyclyloxy group each of which can be optionally substituted; or R$_3$-R$_{10}$ are selected from non-hydrogen substituents, including halogens (e.g., Br—, I—, Cl—, F—), hydroxyl (—OH), nitro groups (—NO$_2$), cyano (—CN) isocyano (—NC), thiocyano (—SCN), isothiocyano (—NCS), sulfuryl (—SO$_2$), —N(R')$_2$, —COR', —COOR', —CON(R')$_2$, —NR'—CO—R', —NR'—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, heterocyclic groups, each of which groups is optionally substituted particularly with one or more halogen, hydroxyl, amino, alkylamino, or dialkylamino groups; or two of R$_3$-R$_{10}$ are linked together to form an optionally substituted carbocyclic, aryl, heterocyclic or heteroaryl ring wherein one or two carbons of the ring can be replaced with —CO— and the carbocyclic or heterocyclic rings can be saturated or unsaturated.

In a specific embodiment of formula II, all of R$_3$-R$_{10}$ are hydrogens. In a specific embodiment of formula II, all except one of R$_3$-R$_{10}$ are hydrogens. In a specific embodiment, one or more of R$_3$-R$_{10}$ are selected from hydrogen, alkyl groups having 1-3 carbon atoms, halogens, —N(R')$_2$, —COR', —COOR', —CON(R')$_2$, —NR'—CO—R', —NR'—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, heterocyclic groups, each of which groups is optionally substituted particularly with one or more halogen, hydroxyl, amino, alkylamino, or dialkylamino groups. In a specific embodiment, one or more of R$_3$-R$_{10}$ is a —NR'—CO—R' group. In a specific embodiment, one or both of R$_4$ and R$_9$ are —NR'—CO—R' groups. In specific embodiments, the —NR'—CO—R' groups are —NH—CO—R' groups where R' is an alkyl group or a haloalkyl group, and more specifically where R' is a methyl group or a trifluormethyl group.

In a specific embodiment of formula III, R$_2$ is alkyl, alkenyl, alkynyl, or alkoxy. In a specific embodiment of formula III, R$_2$ is carbocyclic. In a specific embodiment of formula III, R$_2$ is aryloxy. In a specific embodiment of formula III, R$_2$ is alkyl which is substituted with a substituent selected from —N(R')$_2$, —COR', —COOR', —CON(R')$_2$, —NR'—CO—R', —NR'—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, heterocyclic groups, each of which groups is optionally substituted particularly with one or more halogen, hydroxyl, amino, alkylamino, or dialkylamino groups.

In a specific embodiment of formula III or IIIA, all of R$_3$-R$_7$ are hydrogens. In a specific embodiment of formula III, all except one of R$_3$-R$_7$ are hydrogens. In a specific embodiment, one or more of R$_3$-R$_7$ are selected from hydrogen, alkyl groups having 1-3 carbon atoms, halogens, —N(R')$_2$, —COR', —COOR', —CON(R')$_2$, —NR'—CO—R', —NR'—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, heterocyclic groups, each of which groups is optionally substituted particularly with one or more halogen, hydroxyl, amino, alkylamino, or dialkylamino groups. In a specific embodiment, one or more of R$_3$-R$_7$ is a —NR'—CO—R' group. In a specific embodiment, one of R$_3$-R$_7$ are —NR'—CO—R' groups. In specific embodiments, the —NR'—CO—R' groups are —NH—COR' groups where R' is an alkyl group or a haloalkyl group, and more specifically where R' is a methyl group or a trifluormethyl group.

Additional diazo-compounds which exhibit high efficiency and high selectivity for esterification, particularly in aqueous solutions include compounds of formula IV:

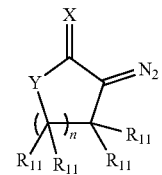

where X is —O— or —S—, Y is —O—, —S— or —NR''—, where R'' is hydrogen or an alkyl group;

n is 1-5; and each R$_{11}$ is independently hydrogen; optionally substituted alkyl; optionally substituted carbocyclic; optionally substituted heterocyclic; —N(R')$_2$—COR'—COOR', —CON(R')$_2$, —NR'—CO—R', —NR'—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, heterocyclic groups, each of which groups is optionally substituted particularly with one or more halogen, hydroxyl, amino, alkylamino, or dialkylamino groups; or two or three R$_{11}$ together form a 3-8 member carbocyclic or heterocyclic ring in which one or two carbons are optionally replaced with —CO— and which rings can be saturated or unsaturated. In a specific embodiment of formula IV, X is O. In a specific embodiment of formula IV, Y is O. In a specific embodiment of formula IV, each $R_{11}$ is selected from hydrogen or an alkyl group having 1-3 carbon atoms. In a specific embodiment of formula IV, n is 1 or 2.

Additional diazo-compounds which exhibit high efficiency and high selectivity esterification, particularly in aqueous solutions include compounds of formula V:

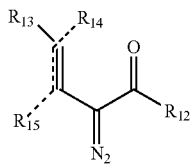

where:
the dotted lines indicate that the bond may be a double bond or a triple bond; if the bond is a double bond then $R_{14}$ and $R_{15}$ are present, if the bond is a triple bond $R_{14}$ and $R_{15}$ are absent; $R_{13}$-$R_{15}$ are selected from hydrogen, halogen, alkyl, alkenyl, alkynyl, alkoxy, aryl, aryloxy, carbocyclic, carbocyclyloxy, heteroaryl, heteroaryloxy, heterocyclyl, or heterocyclyloxy, each of which groups is optionally substituted; and $R_{12}$ is selected from hydrogen, alkyl, alkenyl, alkynyl, alkoxy, aryl, aryloxy, carbocyclic, carbocyclyloxy, heteroaryl, heteroaryloxy, heterocyclyl, or heterocyclyloxy, each of which groups is optionally substituted.

In specific embodiments of formula V, $R_{15}$ is hydrogen or an alkyl group having 1-3 carbon atoms. In specific embodiments of formula V, one of $R_{13}$ or $R_{14}$ is hydrogen. In specific embodiments, one of $R_{13}$ or $R_{14}$ is an optionally substituted alkyl group or an optionally substituted arylalkyl group.

The terms alkyl or alkyl group refer to a monoradical of a straight-chain or branched saturated hydrocarbon. Alkyl groups include straight-chain and branched alkyl groups. Unless otherwise indicated alkyl groups have 1-20 carbon atoms (C1-C20 alkyl groups) and preferred are those that contain 1-10 carbon atoms (C1-C10 alkyl groups) and more preferred are those that contain 1-6 carbon atoms (C1-C6 alkyl groups) and. those that contain 1-3 carbon atoms (C1-C3 alkyl groups) Alkyl groups are optionally substituted with one or more non-hydrogen substituents as described herein. Exemplary alkyl groups include methyl, ethyl, n-propyl, iso-propyl, n-butyl, s-butyl, t-butyl, n-pentyl, branched-pentyl, n-hexyl, branched hexyl, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl.

A carbocyclyl group is a group having one or more saturated or unsaturated carbon rings. Carbocyclyl groups, for example, contain one or two double bonds. One or more carbons in a carbocyclic ring can be —CO— groups. Carbocyclyl groups include those having 3-12 carbon atoms, and optionally replacing 1 or 2 carbon atoms with a —CO— group and optionally having 1, 2 or 3 double bonds. Carbocyclyl groups include those having 5-6 ring carbons. Carbocyclyl groups can contain one or more rings each of which is saturated or unsaturated. Carbocyclyl groups include bicyclic and tricyclic groups. Preferred carbocyclic groups have a single 5- or 6-member ring. Carbocyclyl groups are optionally substituted as described herein. Specifically, carbocyclic groups can be substituted with one or more alkyl groups. Carbocyclyl groups include among others cycloalkyl and cycloalkenyl groups.

Cycloalkyl groups include those which have 1 ring or which are bicyclic or tricyclic. In specific embodiments, cycloalkyl groups have 1 ring having 5-8 carbon atoms and preferably have 5 or 6 carbon atoms.

Cycloalkenyl groups include those which have 1 ring or which are bicyclic or tricyclic and which contain 1-3 double bond. In specific embodiments, cycloalkenyl groups have 1 ring having 5-8 carbon atoms and preferably have 5 or 6 carbon atoms and have one double bond.

A heterocyclyl group is a group having one or more saturated or unsaturated carbon rings and which contains one to three heteroatoms (e.g., N, O or S) per ring. These groups optionally contain one, two or three double bonds. To satisfy valence requirement, a ring atom may be substituted as described herein. One or more carbons in the heterocyclic ring can be —CO— groups. Heterocyclyl groups include those having 3-12 carbon atoms, and 1-6, heteroatoms, wherein 1 or 2 carbon atoms are replaced with a —CO— group. Heterocyclyl groups include those having 3-12 or 3-10 ring atoms of which up to three can be heteroatoms other than carbon. Heterocyclyl groups can contain one or more rings each of which is saturated or unsaturated. Heterocyclyl groups include bicyclic and tricyclic groups. Preferred heterocyclyl groups have 5- or 6-member rings. Heterocyclyl groups are optionally substituted as described herein. Specifically, heterocyclic groups can be substituted with one or more alkyl groups. Heterocyclyl groups include those having 5- and 6-member rings with one or two nitrogens and one or two double bonds. Heterocyclyl groups include those having 5- and 6-member rings with an oxygen or a sulfur and one or two double bonds. Heterocyclyl group include those having 5- or 6-member rings and two different heteroatom, e.g., N and O, O and S or N and S. Specific heterocyclyl groups include among others among others, pyrrolidinyl, piperidyl, piperazinyl, pyrrolyl, pyrrolinyl, furyl, thienyl, morpholinyl, oxazolyl, oxazolinyl, oxazolidinyl, indolyl, triazoly, and triazinyl groups.

Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups are optionally substituted with one or more non-hydrogen substituents. Substituted aryl groups include among others those which are substituted with alkyl or alkenyl groups, which groups in turn can be optionally substituted. Specific aryl groups include phenyl groups, biphenyl groups, and naphthyl groups, all of which are optionally substituted as described herein. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogen replaced with one or more fluorine atoms.

Heteroaryl groups include groups having one or more aromatic rings in which at least one ring contains a heteroatom (a non-carbon ring atom). Heteroaryl groups include those having one or two heteroaromatic rings carrying 1, 2 or 3 heteroatoms and optionally have one 6-member aromatic ring. Heteroaryl groups can contain 5-20, 5-12 or 5-10 ring atoms. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two 0, and those with one or two S, or combinations of one or two or three N, O or S. Specific heteroaryl groups include furyl, pyridinyl, pyrazinyl, pyrimidinyl, quinolinyl, and purinyl groups. In specific embodiments herein aryl groups contain no heteroatoms in the aryl rings. Aryl including heteroaryl groups are optionally substituted.

Heteroatoms include O, N, S, P or B. More specifically heteroatoms are N, O or S. In specific embodiments, one or more heteroatoms are substituted for carbons in aromatic or carbocyclic rings. To satisfy valence any heteroatoms in such aromatic or carbocyclic rings may be bonded to H or a substituent group, e.g., an alkyl group or other substituent.

Arylalkyl groups are alkyl groups substituted with one or more aryl groups wherein the alkyl groups optionally carry additional substituents and the aryl groups are optionally substituted. Exemplary arylalkyl groups are benzyl groups.

Heteroarylalkyl groups are alkyl groups substituted with one or more heteroaryl groups wherein the alkyl groups optionally carry additional substituents and the aryl groups are optionally substituted.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl.

Alkylheteroaryl groups are heteroaryl groups substituted with one or more alkyl groups wherein the alkyl groups optionally carry additional substituents and the aryl groups are optionally substituted.

An alkoxy group is an alkyl group, as broadly discussed above, linked to oxygen ($R_{alkyl}$—O—). An aryloxy group is an aryl group, as discussed above, linked to an oxygen ($R_{aryl}$—O—). A heteroaryloxy group is a heteroaryl group as discussed above linked to an oxygen ($R_{heteroaryl}$—O—). A carbocyclyloxy group is an carbocyclyl group, as broadly discussed above, linked to oxygen ($R_{carbocyclyl}$—O—). A heterocyclyloxy group is an carbocyclyl group, as broadly discussed above, linked to oxygen ($R_{heterocyclyl}$—O—).

An acyl group is an R'—CO group where R' in general is a hydrogen, an alkyl, alkenyl or alkynyl, aryl or heteroaryl group as described above. In specific embodiments, acyl groups have 1-20, 1-12 or 1-6 carbon atoms and optionally 1-3 heteroatom, optionally one double bond or one triple bond. In specific embodiments, R is a C1-C6 alkyl, alkenyl or alkynyl group. cyclic configuration or a combination thereof, attached to the parent structure through a carbonyl functionality. Examples include acetyl, benzoyl, propionyl, isobutyryl, or oxalyl. The R' group of acyl groups are optionally substituted as described herein. When R' is hydrogen, the group is a formyl group. An acetyl group is a $CH_3$—CO— group. Another exemplary acyl group is a benzyloxy group.

An alkylthio group is an alkyl group, as broadly discussed above, linked to a sulfur ($R_{alkyl}$—S—) An arylthio group is an aryl group, as discussed above, linked to a sulfur ($R_{aryl}$—S—). A heteroarylthio group is a heteroaryl group as discussed above linked to an sulfur ($R_{heteroaryl}$—S—). A carbocyclylthio group is an carbocyclyl group, as broadly discussed above, linked to oxygen ($R_{carbocyclyl}$—S—). A heterocyclylthio group is an carbocyclyl group, as broadly discussed above, linked to oxygen ($R_{heterocyclyl}$—S—).

The term amino group is refer to the species —N(H)$_2$—. The term alkylamino refers to the species —NHR" where R" is an alkyl group, particularly an alkyl group having 1-3 carbon atoms. The term dialkylamino refers to the species —NR"$_2$ where each R" is independently an alkyl group, particularly an alkyl group having 1-3 carbon atoms.

Groups herein are optionally substituted most generally alky, alkenyl, alkynyl, and aryl, heteroaryl, carbocyclyl, and heterocyclyl groups can be substituted, for example, with one or more oxo group, thioxo group, halogen, nitro, cyano, cyanate, azido, thiocyano, isocyano, isothiocyano, sulfhydryl, hydroxyl, alkyl, alkoxy, alkenyl, alkenyloxy, alkynyl, alkynyloxy, aryl, aryloxy, heteroaryl, heteroaryloxy, carbocyclyl, carbocyclyloxy, heterocyclyl, heterocyclyloxy, alkylthio, alkenylthio, alkynylthio, arylthio, thioheteroaryl, thioheteroaryl, thiocarbocyclyl, thioheterocyclyl, —COR, —COH, —OCOR, —OCOH, —CO—OR, —CO—OH, —CO—O—CO—R, —CON(R)$_2$, —CONHR, —CONH$_2$, —NR—COR, —NHCOR, —NHR, —N(R)$_2$, —O—SO$_2$—R, —SO$_2$—R, —SO$_2$—NHR, —SO$_2$—N(R)$_2$, —NR—SO$_2$—R, —NH—SO$_2$—R, —NRCO—N(R)$_2$, —NH—CO—NHR, —O—PO(OR)$_2$, —O—PO(OR)(N(R)$_2$), —O—PO(N(R)$_2$)$_2$, —N—PO(OR)$_2$, —N—PO(OR)(N(R)$_2$), —P(R)$_2$, —B(OH)$_2$, —B(OH)(OR), —B(OR)$_2$, where each R independently is an organic group and more specifically is an alkyl, alkenyl, alkynyl, aryl, heteroaryl, carbocyclyl, or heterocyclyl group or two R within the same substituent can together form a carbocyclic or heterocyclic ring having 3 to 10 ring atoms. Organic groups of non-hydrogen substituents are in turn optionally substituted with one or more halogens, nitro, cyano, isocyano, isothiocyano, hydroxyl, sulfhydryl, haloalkyl, hydroxyalkyl, amino, alkylamino, dialkylamino, arylalkyl, unsubstituted alkyl, unsubstituted alkenyl, unsubstituted alkynyl alkylalkenyl, alkylalkynyl, haloaryl, hydroxylaryl, alkylaryl, unsubstituted aryl, unsubstituted carbocylic, halo-substituted carbocyclic, hydroxyl-substituted carbocyclic, alkyl-substituted carbocyclic, unsubstituted heterocyclic, unsubstituted heteroaryl, alkyl-substituted heteroaryl, or alkyl-substituted heterocyclic. In specific embodiments, R groups of substituents are independently selected from alkyl groups, haloalkyl groups, phenyl groups, benzyl groups and halo-substituted phenyl and benzyl groups. In specific embodiments, non-hydrogen substituents have 1-20 carbon atoms, 1-10 carbon atoms, 1-7 carbon atoms, 1-5 carbon atoms or 1-3 carbon atoms. In specific embodiments, non-hydrogen substituents have 1-10 heteroatoms, 1-6 heteroatoms, 1-4 heteroatoms, or 1, 2, or 3 heteroatoms. Heteroatoms include O, N, S, P, B and Se and preferably are 0, N or S.

In specific embodiments, optional substitution is substitution with 1-12 non-hydrogen substituents. In specific embodiments, optional substitution is substitution with 1-6 non-hydrogen substituents. In specific embodiments, optional substitution is substitution with 1-3 non-hydrogen substituents. In specific embodiments, optional substituents contain 6 or fewer carbon atoms. In specific embodiments, optional substitution is substitution by one or more halogen, hydroxyl group, cyano group, oxo group, thioxo group, unsubstituted C1-C6 alkyl group or unsubstituted aryl group. The term oxo group and thioxo group refer to substitution of a carbon atom with a=O or a =S to form respectively —CO— (carbonyl) or —CS— (thiocarbonyl) groups.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Compounds of the invention may contain chemical groups (acidic or basic groups) that can be in the form of salts. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Salts of the invention include "pharmaceutically acceptable salts" which refers to those salts which retain the biological effectiveness and properties of the free bases or free acids, and which are not biologically or otherwise undesirable. Pharmaceutically acceptable salts comprise pharmaceutically-acceptable anions and/or cations.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

With respect to the various compounds of the invention, the atoms therein may have various isotopic forms, e.g., isotopes of hydrogen include deuterium and tritium. All isotopic variants of compounds of the invention are included within the invention and particularly included at deuterium and $^{13}C$ isotopic variants. It will be appreciated that such isotopic variants may be useful for carrying out various chemical and biological analyses, investigations of reaction mechanisms and the like. Methods for making isotopic variants are known in the art.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

General Methods:

Reagent chemicals were obtained from commercial sources and used without further purification. All glassware was flame-dried under vacuum, and reactions were performed under $N_2(g)$ unless indicated otherwise. Dichloromethane, diethyl ether, tetrahydrofuran, and toluene were dried over a column of alumina. Dimethylformamide and triethylamine were dried over alumina and purified further by passage through an isocyanate scrubbing column. Flash chromatography was performed with columns of 40-63 Å silica gel, 230-400 mesh (Silicycle, Quebec City, Canada). Thin-layer chromatography (TLC) was performed on plates of EMD 250-μm silica 60-F254. The phrase "concentrated under reduced pressure" refers to the removal of solvents and other volatile materials using a rotary evaporator at water aspirator pressure (<20 torr) while maintaining the water-bath temperature below 40° C. Residual solvent was removed from samples at high vacuum (<0.1 torr). The term "high vacuum" refers to vacuum achieved by mechanical belt-drive oil pump. All NMR spectra were acquired at ambient temperature with a Bruker DMX-400 Avance, Bruker Avance III 500i with cryoprobe, or Bruker Avance III 500ii with cryoprobe spectrometer at the National Magnetic Resonance Facility at Madison (NMRFAM), and were referenced to TMS or a residual protic solvent. Electrospray ionization (ESI) mass spectrometry was performed with a Micromass LCT at the Mass Spectrometry Facility in the Department of Chemistry at the University of Wisconsin-Madison.

Example 1: Esterification Reactions in Acetonitrile

The reactivity of moderately-stabilized diazo compounds 1 and 2 with various carboxylic acids was examined to gain a better understanding of how the electronic structure of the diazo compound affects reaction efficiency. The reactivity of compounds 1 and 2 with carboxylic acids of varying acidity and bearing a variety of reactive functional groups was studied in acetonitrile (Scheme 1). Regardless of steric hindrance or pKa of the carboxylic acid, higher yields and faster reaction times were observed for diazofluorene 2 than with diazoacetamide 1. In addition, both diazo compounds were unreactive toward the other common functional groups present in biological systems such as alcohols, amines, and thiols. Interestingly 1-alanine (h) proved unreactive with either diazo compound under any conditions tested; its zwitterionic character precludes the initial protonation event. [21] This lack of reactivity displays the subtle importance of diazo basicity in determining esterification efficiency. While a carboxylic acid is acidic enough to promote the reaction, a protonated ammonium ion lacks sufficient acidity to allow the reaction to proceed at an appreciable rate.

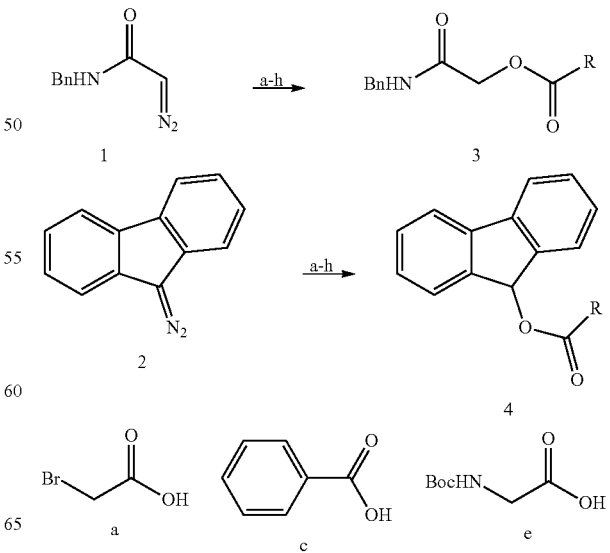

Scheme 1

-continued

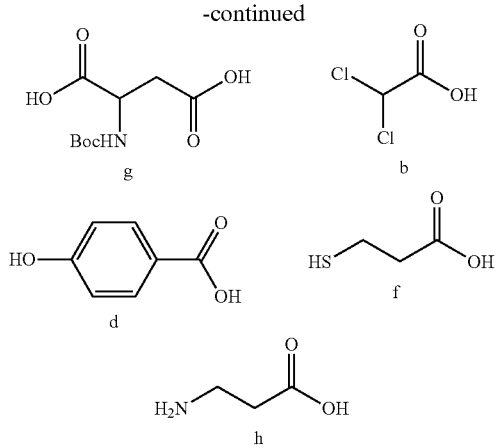

-continued

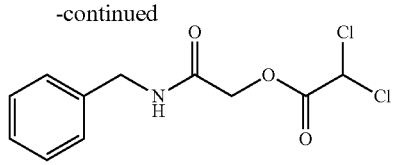

Diazobenzylacetamide (0.010 g, 0.057 mmol) was added to a solution of dichloroacetic acid (0.005 mL, 0.057 mmol) in anhydrous acetonitrile (0.57 mL) and the reaction was allowed to stir ½ hour at room temperature until determined to be complete by thin-layer chromatography ($R_f$=0.3 in 30% EtOAc, 70% hexanes). The reaction was concentrated and purified by silica gel chromatography to give benzyl-acetamido-dichloroacetate (0.008 g, 51%).

$^1$H NMR (500 MHz, CDCl$_3$) δ 7.43-7.29 (m, 5H), 6.38 (bs, 1H), 6.05 (s, 1H), 4.83 (s, 2H), 4.56 (d, J=5.8 Hz, 2H). $^{13}$C NMR (126 MHz, CDCl$_3$) δ 165.5, 163.1, 137.3, 129.1, 128.1, 128.0, 64.9, 63.9, 43.6. HRMS (ESI) m/z 293.0459 [calc'd for C$_{11}$H$_{15}$Cl$_2$N$_2$O$_3$ (M+NH$_4^+$) 293.0455].

|  | Acid | | | | | | | | | | | | | | |
|---|---|---|---|---|---|---|---|---|---|---|---|---|---|---|---|
|  | a | | b | | c | | d | | e | | f | | g | | h |
| Diazo | 1 | 2 | 1 | 2 | 1 | 2 | 1 | 2 | 1 | 2 | 1 | 2 | 1 | 2 | 1 | 2 |
| Time (min) | 60 | 20 | 30 | 1 | 480 | 300 | 720 | 600 | 180 | 120 | 720 | 480 | 720 | 300 | N/R | N/R |
| Yield (%) | 74 | 94 | 51 | 91 | 78 | 90 | 61 | 85 | 82 | 85 | 76 | 80 | 63 | 89 | | |

Diazobenzylacetamide Reactions

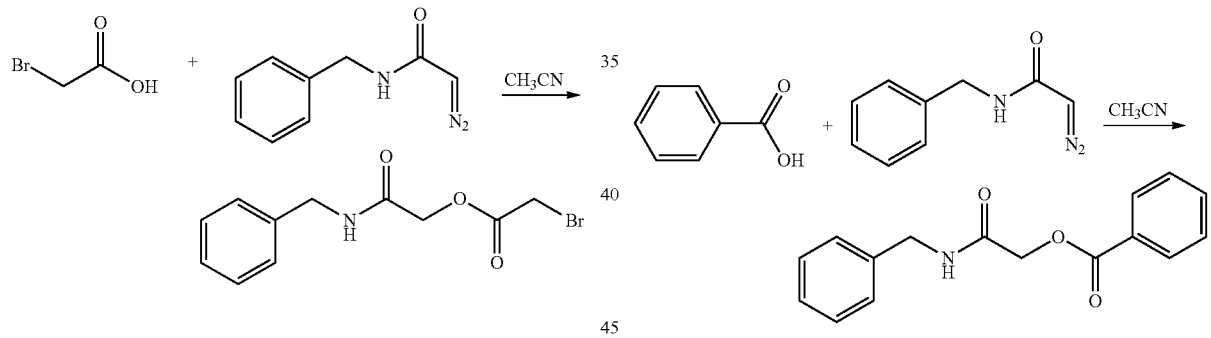

Diazobenzylacetamide (0.010 g, 0.057 mmol) was added to a solution of bromoacetic acid (0.008 g, 0.057 mmol) in anhydrous acetonitrile (0.57 mL) and the reaction was allowed to stir 1 hour at room temperature until determined to be complete by thin-layer chromatography (Rf=0.3 in 50% EtOAc, 50% hexanes). The reaction was concentrated and purified by silica gel chromatography to give N-benzyl-acetamido-bromoacetate (0.012 g, 74%).

$^1$H NMR (400 MHz, CDCl$_3$) δ 7.38-7.16 (m, 5H), 6.41 (bs, 1H), 4.70 (s, 2H), 4.50 (d, J=5.9 Hz, 2H), 3.87 (s, 2H). $^{13}$C NMR (126 MHz, CDCl$_3$) δ 166.3, 165.9, 137.5, 129.1, 129.0, 128.0, 78.0, 64.1, 43.5, 25.2. HRMS (ESI) m/z 286.0074 [calc'd for C$_{11}$H$_{13}$BrNO$_3$ (M+H$^+$) 286.0074].

Diazobenzylacetamide (0.010 g, 0.057 mmol) was added to a solution of benzoic acid (0.007 g, 0.057 mmol) in anhydrous acetonitrile (0.57 mL) and the reaction was allowed to stir 8 hours at room temperature until determined to be complete by thin-layer chromatography ($R_f$=0.8 in 80% EtOAc, 20% hexanes). The reaction was concentrated and purified by silica gel chromatography to give benzyl-acetamido-benzoate (0.012 g, 78%).

$^1$H NMR (400 MHz, CDCl$_3$) δ 8.02 (d, J=7.6 Hz, 2H), 7.59 (t, J=7.3 Hz, 1H), 7.45 (t, J=7.6 Hz, 2H), 7.39-7.21 (m, 5H), 6.42 (bs, 1H), 4.87 (s, 2H), 4.53 (d, J=6.0 Hz, 2H). $^{13}$C NMR (126 MHz, CDCl$_3$) δ 167.3, 165.4, 137.8, 134.0, 134.0, 130.0, 129.0, 128.9, 127.9, 127.9, 63.7, 43.3. HRMS (ESI) m/z 270.1133 [calc'd for C$_{16}$H$_{16}$NO$_3$ (M+H$^+$) 270.1125].

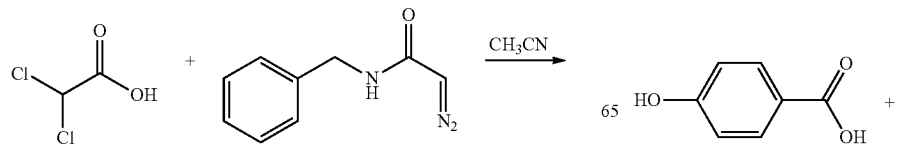

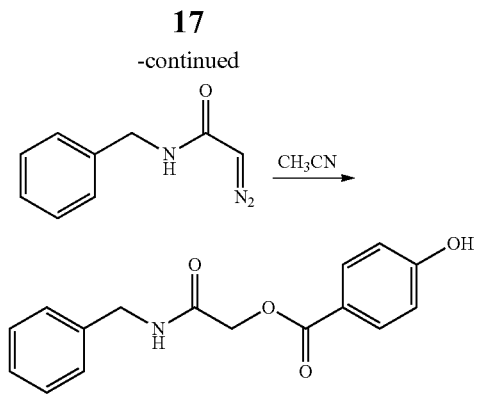

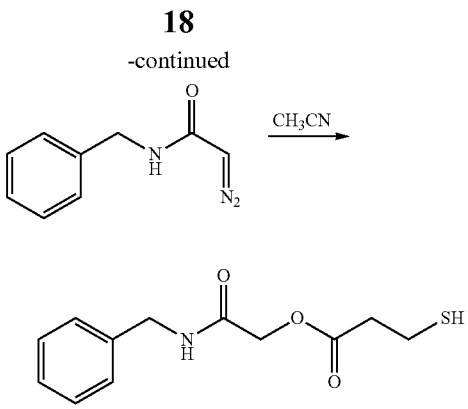

Diazobenzylacetamide (0.010 g, 0.057 mmol) was added to a solution of 4-hydroxybenzoic acid (0.008 g, 0.057 mmol) in anhydrous acetonitrile (0.57 mL) and the reaction was allowed to stir 12 hours at room temperature until determined to be complete by thin-layer chromatography ($R_f$=0.6 in 75% EtOAc, 25% hexanes). The reaction was concentrated and purified by silica gel chromatography to give benzyl-acetamido-4-hydroxybenzoate (0.011 g, 61%).

$^1$H NMR (700 MHz, CDCl$_3$) δ 7.98 (d, J=8.7 Hz, 2H), 7.40-7.35 (m, 2H), 7.36-7.31 (m, 3H), 6.90 (d, J=8.7 Hz, 2H), 6.45 (bs, 1H), 4.89 (s, 2H), 4.58 (d, J=5.9 Hz, 2H). $^{13}$C NMR (126 MHz, CDCl$_3$) δ 167.6, 165.0, 160.5, 137.8, 132.4, 129.0, 127.9, 127.9, 121.6, 115.7, 63.5, 43.3. HRMS (ESI) m/z 286.1070 [calc'd for C$_{16}$H$_{16}$NO$_4$ (M+H$^+$) 286.1074].

Diazobenzylacetamide (0.010 g, 0.057 mmol) was added to a solution of 3-mercaptopropanoic acid (0.005 mL, 0.057 mmol) in anhydrous acetonitrile (0.57 mL) and the reaction was allowed to stir 12 hours at room temperature until determined to be complete by thin-layer chromatography ($R_f$=0.6 in 70% EtOAc, 30% hexanes). The reaction was concentrated and purified by silica gel chromatography to give benzyl-acetamido-3-mercaptopropanoate (0.011 g, 76%).

$^1$H NMR (400 MHz, CDCl$_3$) δ 7.46-7.13 (m, 5H), 6.54 (bs, 1H), 4.69 (s, 2H), 4.50 (d, J=5.7 Hz, 2H), 2.82-2.77 (m, 2H), 2.76-2.71 (m, 2H), 1.59 (t, J=8.1 Hz, 1H). $^{13}$C NMR (126 MHz, CDCl$_3$) δ 170.5, 166.9, 137.7, 129.0, 128.1, 128.0, 63.4, 43.4, 38.3, 20.0. HRMS (ESI) m/z 271.1115 [calc'd for C$_{12}$H$_{19}$N$_2$O$_3$S (M+NH$_4^+$) 271.1111].

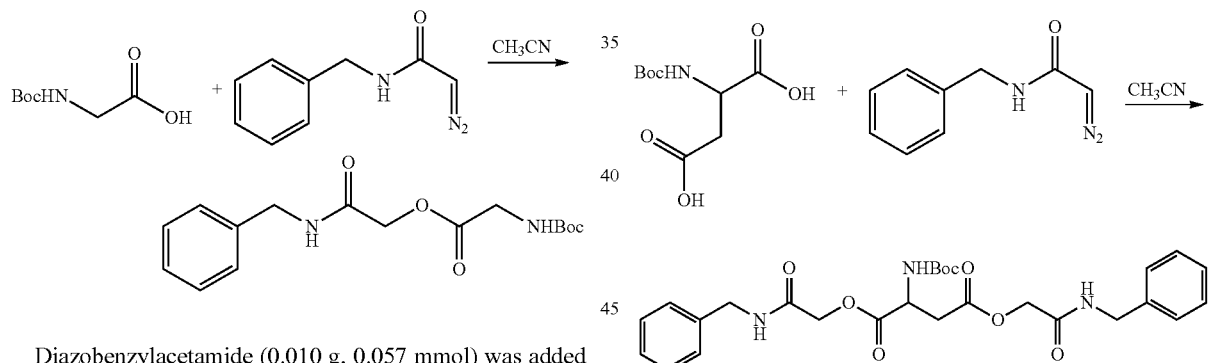

Diazobenzylacetamide (0.010 g, 0.057 mmol) was added to a solution of Boc-protected glycine (0.010 g, 0.057 mmol) in anhydrous acetonitrile (0.57 mL) and the reaction was allowed to stir 3 hours at room temperature until determined to be complete by thin-layer chromatography ($R_f$=0.7 in 75% EtOAc, 25% hexanes). The reaction was concentrated and purified by silica gel chromatography to give benzyl-acetamido-Boc-protected glycine (0.015 g, 82%).

$^1$H NMR (400 MHz, CDCl$_3$) δ 7.38-7.25 (m, 5H), 7.07 (bs, 1H), 5.10 (bs, 1H), 4.71 (s, 2H), 4.48 (d, J=6.0 Hz, 2H), 3.90 (d, J=5.9 Hz, 2H), 1.37 (s, 9H). $^{13}$C NMR (126 MHz, CDCl$_3$) δ 169.1, 166.8, 156.4, 137.8, 128.7, 127.8, 127.5, 80.8, 63.2, 43.1, 42.9, 28.2. HRMS (ESI) m/z 340.1873 [calc'd for C$_{16}$H$_{26}$N$_3$O$_5$ (M+NH$_4^+$) 340.1867].

Diazobenzylacetamide (0.020 g, 0.114 mmol) was added to a solution of Boc-protected aspartic acid (0.013 g, 0.057 mmol) in anhydrous acetonitrile (0.57 mL) and the reaction was allowed to stir 12 hours at room temperature until determined to be complete by thin-layer chromatography ($R_f$=0.5 in 80% EtOAc, 20% hexanes). The reaction was concentrated and purified by silica gel chromatography to give bis-benzyl-acetamido-Boc-protected aspartate (0.019 g, 63%).

$^1$H NMR (400 MHz, CDCl$_3$) δ 7.38-7.20 (m, 10H), 7.04 (bs, 1H), 6.49 (bs, 1H), 5.53 (bs, 1H), 4.73-4.55 (m, 3H), 4.53-4.35 (m, 6H), 3.03 (dd, J=16.9, 5.2 Hz, 1H), 2.94 (dd, J=16.9, 5.2 Hz, 1H), 1.34 (s, 9H). $^{13}$C NMR (126 MHz, CDCl$_3$) δ 170.3, 170.3, 166.5, 166.2, 155.7, 137.7, 137.5, 128.8, 128.6, 127.9, 127.8, 127.8, 127.5, 81.1, 63.8, 63.4, 50.3, 43.2, 43.1, 36.4, 28.2. HRMS (ESI) m/z 545.2632 [calc'd for C$_{27}$H$_{37}$N$_4$O$_8$ (M+NH$_4^+$) 545.2606].

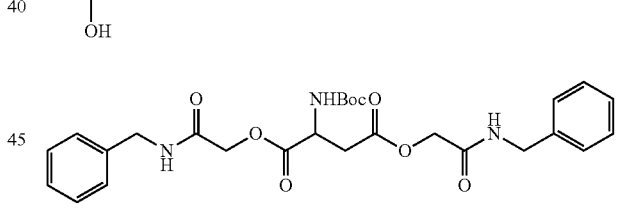

Diazofluorene Reactions

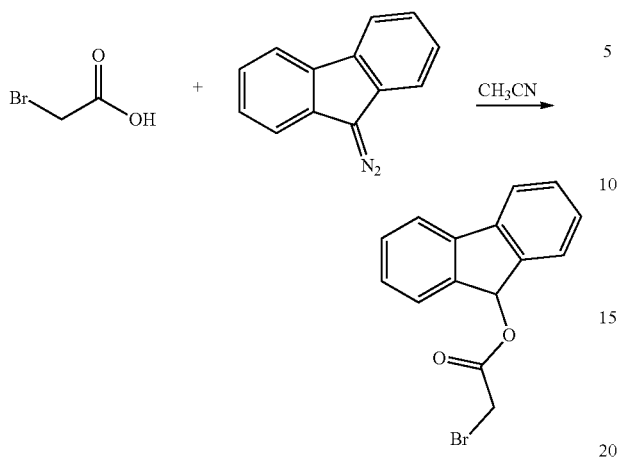

Diazofluorene (0.003 g, 0.016 mmol) was added to a solution of bromoacetic acid (0.002 g, 0.016 mmol) in anhydrous acetonitrile (0.16 mL) and the reaction was allowed to stir 20 minutes at room temperature until determined to be complete by thin-layer chromatography ($R_f$=0.7 in 30% EtOAc, 70% hexanes). The reaction was concentrated and purified by silica gel chromatography to give fluorenyl-bromoacetate (0.004 g, 94%).

$^1$H NMR (400 MHz, CDCl$_3$) δ 7.66 (d, J=7.5 Hz, 2H), 7.54 (d, J=7.5 Hz, 2H), 7.41 (t, J=7.5 Hz, 2H), 7.29 (t, J=7.5 Hz, 2H), 6.80 (s, 1H), 3.92 (s, 2H). $^{13}$C NMR (126 MHz, CDCl$_3$) δ 168.4, 141.3, 141.3, 130.1, 128.2, 126.2, 120.4, 26.1. [Fluorenyl alkyl CH overlaps with a chloroform peak]. $^{13}$C NMR (126 MHz, CD$_3$OD) δ 170.1, 142.9, 142.5, 131.0, 129.2, 127.1, 121.3, 77.9, 26.7. HRMS (EI) m/z 301.9926 [calc'd for C$_{15}$H$_{11}$BrO$_2$ (M$^+$) 301.9937].

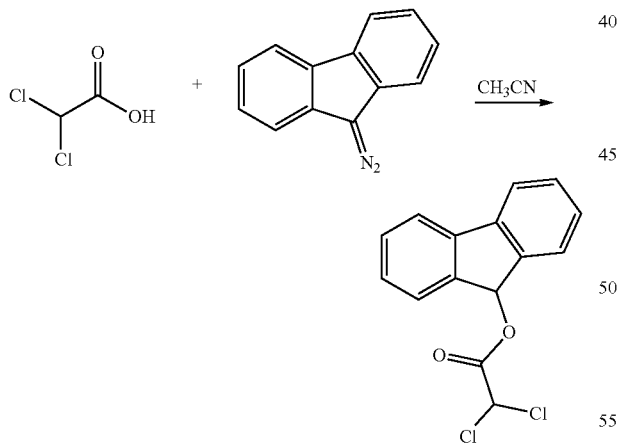

Diazofluorene (0.003 g, 0.016 mmol) was added to a solution of dichloroacetic acid (0.002 g, 0.016 mmol) in anhydrous acetonitrile (0.16 mL) and the reaction was allowed to stir 1 minute at room temperature until determined to be complete by thin-layer chromatography ($R_f$=0.7 in 30% EtOAc, 70% hexanes). The reaction was concentrated and purified by silica gel chromatography to give fluorenyl-dichloroacetate (0.004 g, 91%).

$^1$H NMR (400 MHz, CDCl$_3$) δ 7.68 (d, J=7.5 Hz, 2H), 7.56 (d, J=7.5 Hz, 2H), 7.45 (t, J=7.5 Hz, 2H), 7.32 (t, J=7.5 Hz, 2H), 6.83 (s, 1H), 6.03 (s, 1H). $^{13}$C NMR (126 MHz, CDCl$_3$) δ 165.8, 141.4, 140.6, 130.3, 128.4, 126.2, 120.5, 78.1, 64.5. HRMS (EI) m/z 292.0042 [calc'd for C$_{15}$H$_{10}$Cl$_2$O$_2$ (M$^+$) 292.0053].

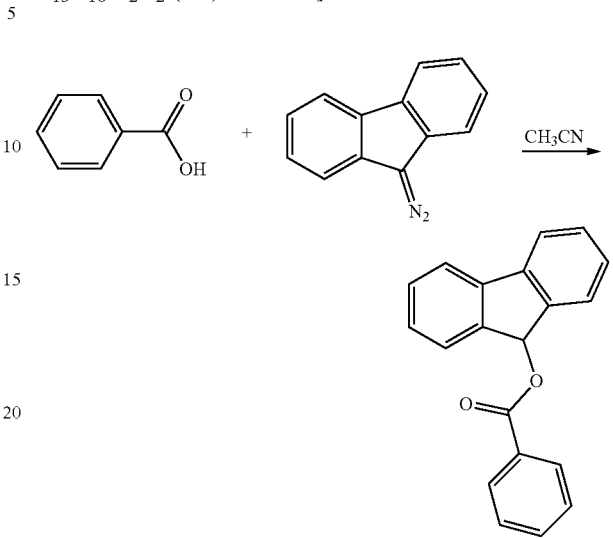

Diazofluorene (0.006 g, 0.031 mmol) was added to a solution of benzoic acid (0.004 g, 0.031 mmol) in anhydrous acetonitrile (0.31 mL) and the reaction was allowed to stir 5 hours at room temperature until determined to be complete by thin-layer chromatography ($R_f$=0.9 in 30% EtOAc, 70% hexanes). The reaction was concentrated and purified by silica gel chromatography to give fluorenyl-benzoate (0.008 g, 90%).

$^1$H NMR (400 MHz, CDCl$_3$) δ 8.09 (d, J=7.5 Hz, 2H), 7.71 (d, J=7.5 Hz, 2H), 7.63 (d, J=7.5 Hz, 2H), 7.57 (t, J=7.7 Hz, 1H), 7.43 (t, J=7.7 Hz, 4H), 7.31 (t, J=7.5 Hz, 2H), 7.05 (s, 1H). $^{13}$C NMR (101 MHz, CDCl$_3$) δ 167.5, 142.4, 141.3, 133.4, 130.2, 130.2, 129.7, 128.6, 128.1, 126.3, 120.3, 75.8. HRMS (ESI) m/z 304.1338 [calc'd for C$_{20}$H$_{18}$NO$_2$ (M+NH$_4^+$) 304.1333].

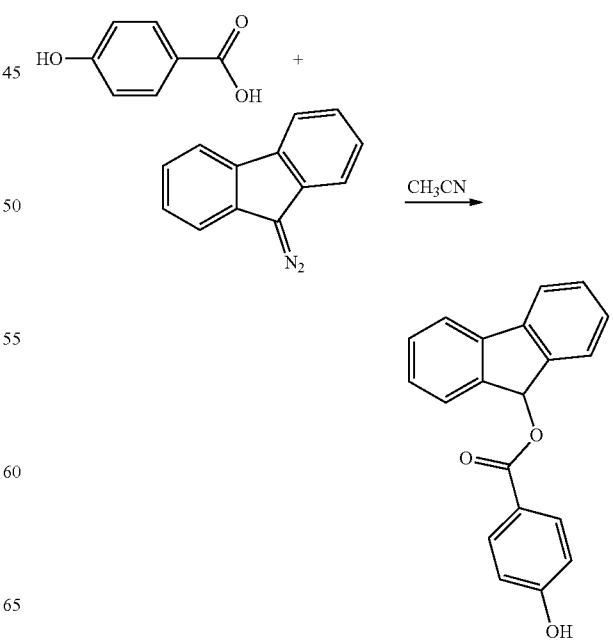

Diazofluorene (0.012 g, 0.063 mmol) was added to a solution of 4-hydroxybenzoic acid (0.009 g, 0.063 mmol) in anhydrous acetonitrile (0.60 mL) and the reaction was allowed to stir 10 hours before being concentrated and the resulting residue was purified by silica gel chromatography to give fluorenyl-4-hydroxybenzoate (0.016 g, 85%).

$^1$H NMR (400 MHz, CDCl$_3$) δ 7.98 (d, J=8.6 Hz, 2H), 7.68 (d, J=7.6 Hz, 2H), 7.60 (d, J=7.6 Hz, 2H), 7.41 (t, J=7.6 Hz, 2H), 7.28 (t, J=7.6 Hz, 2H), 7.00 (s, 1H), 6.82 (d, J=8.6 Hz, 2H). $^{13}$C NMR (126 MHz, CDCl$_3$) δ 167.1, 160.0, 142.5, 141.3, 132.6, 129.7, 128.1, 126.3, 122.9, 120.3, 115.4, 75.6. HRMS (ESI) m/z 320.1293 [calc'd for C$_{20}$H$_{18}$NO$_3$ (M+NH$_4$$^+$) 320.1282].

Diazofluorene (0.018 g, 0.094 mmol) was added to a solution of 3-mercaptopropanoic acid (0.010 g, 0.094 mmol) in anhydrous acetonitrile (0.94 mL) and the reaction was allowed to stir 8 hours at room temperature before being concentrated and the resulting residue was purified by silica gel chromatography to give fluorenyl-3-mercaptopropanoate (0.020 g, 80%).

$^1$H NMR (400 MHz, CDCl$_3$) δ 7.65 (d, J=7.5 Hz, 2H), 7.53 (d, J=7.5 Hz, 2H), 7.40 (t, J=7.5 Hz, 2H), 7.28 (t, J=7.5 Hz, 2H), 6.83 (s, 1H), 2.83 (dd, J=8.2, 6.3 Hz, 2H), 2.76 (t, J=6.3 Hz, 2H), 1.65 (t, J=8.2 Hz, 1H). $^{13}$C NMR (126 MHz, CDCl$_3$) δ 172.6, 142.0, 141.3, 129.8, 128.1, 126.1, 120.3, 75.6, 39.0, 20.2. HRMS (ESI) m/z 288.1059 [calc'd for C$_{16}$H$_{18}$NO$_2$S (M+NH$_4$$^+$) 288.1053].

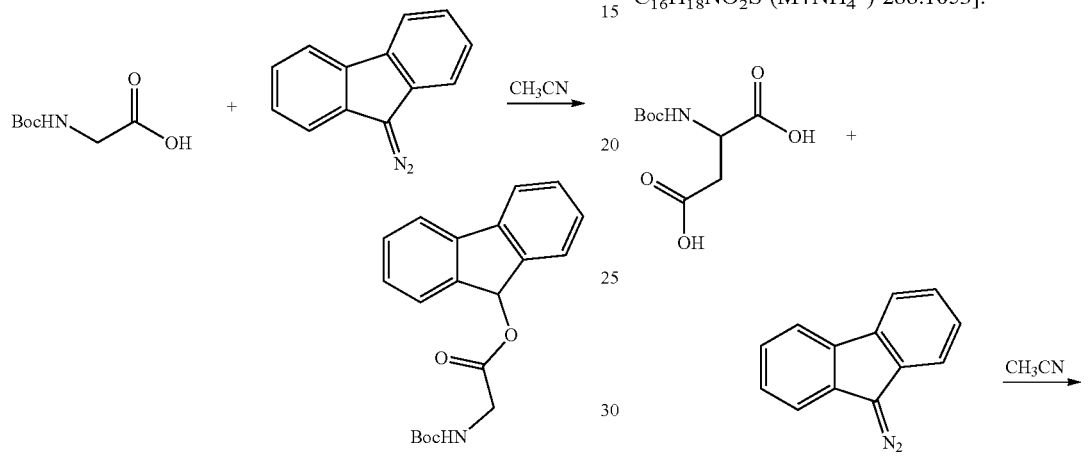

Diazofluorene (0.006 g, 0.031 mmol) was added to a solution of Boc-protected glycine (0.006 g, 0.031 mmol) in anhydrous acetonitrile (0.31 mL) and the reaction was allowed to stir 2 hours until determined to be complete by thin-layer chromatography (R$_f$=0.6 in 30% EtOAc, 70% hexanes). The reaction was concentrated and purified by silica gel chromatography to give fluorenyl-Boc-protected glycine (0.009 g, 85%).

$^1$H NMR (400 MHz, CDCl$_3$) δ 7.65 (d, J=7.5 Hz, 2H), 7.52 (d, J=7.5 Hz, 2H), 7.40 (t, J=7.5 Hz, 2H), 7.28 (t, J=7.5 Hz, 2H), 6.81 (s, 1H), 5.03 (bs, 1H), 4.01 (d, J=5.7 Hz, 2H), 1.44 (s, 9H). $^{13}$C NMR (126 MHz, CDCl$_3$) δ 171.4, 155.9, 141.6, 141.3, 130.0, 128.2, 126.2, 120.3, 80.4, 76.3, 76.2, 43.0, 28.5. HRMS (ESI) m/z 340.1535 [calc'd for C$_{20}$H$_{22}$NO$_4$ (M+H$^+$) 340.1544].

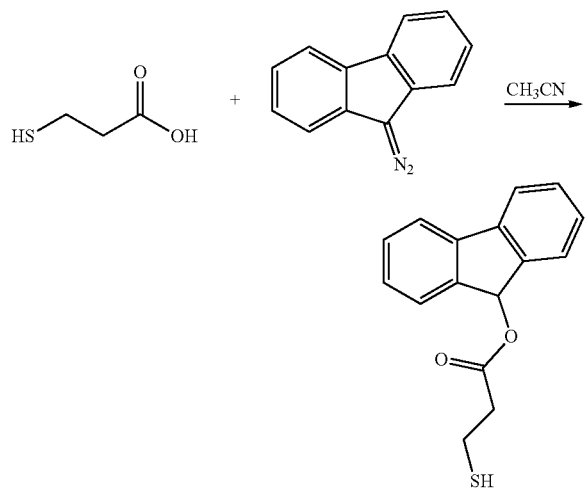

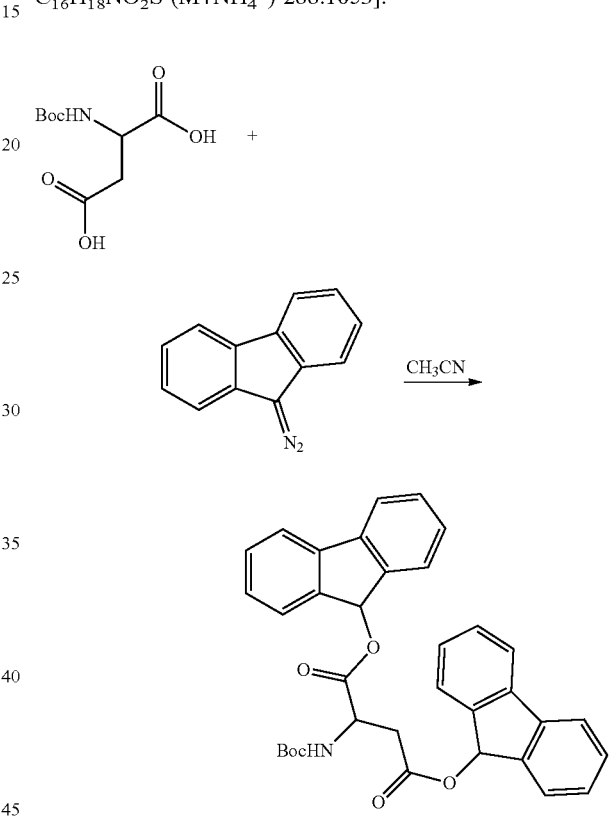

Diazofluorene (0.012 g, 0.063 mmol) was added to a solution of Boc-aspartic acid (0.007 g, 0.0315 mmol) in anhydrous acetonitrile (0.31 mL) and the reaction was allowed to stir 5 hours at room temperature before being concentrated and purified by silica gel chromatography to give bisfluorenyl-Boc-aspartate (0.019 g, 89%).

$^1$H NMR (500 MHz, CDCl$_3$) δ 7.74-7.64 (m, 4H), 7.59-7.51 (m, 4H), 7.50-7.37 (m, 4H), 7.36-7.15 (m, 4H), 6.90 (s, 1H), 6.77 (s, 1H), 5.70 (d, J=8.6 Hz, 1H), 4.83-4.72 (m, 1H), 3.14 (dd, J=17.1, 4.5 Hz, 1H), 3.00 (dd, J=17.1, 4.7 Hz, 1H), 1.49 (s, 9H). $^{13}$C NMR (126 MHz, CDCl$_3$) δ 172.0, 172.0, 155.7, 141.6, 141.5, 141.3, 141.2, 129.9, 129.8, 128.2, 128.1, 126.4, 126.1, 120.3, 120.2, 80.5, 76.4, 75.9, 50.6, 37.2, 28.5. HRMS (ESI) m/z 579.2478 [calc'd for C$_{35}$H$_{35}$N$_2$O$_6$ (M+NH$_4$$^+$) 579.2490].

Example 2: Esterification Screening in Acetonitrile/Buffer Solution

The reactivity difference between diazo-compounds 1 and 2 was further investigated using reactions analogous to those carried out in Example 1 in 3:1 mixtures of acetonitrile and MES buffer (pH=5.5) (Scheme 2). These experiments also specifically addressed the question of chemoselectivity. While diazobenzylacetamide 1 was competent for esterification under these conditions, the major product was the alcohol by-product 5 formed when water attacks the diazonium ion. In contrast, diazofluorene 2 gave primarily the desired ester 4 in all cases. Interestingly the product ratios with 1 varied inconsistently, while they were relatively unchanged with 2 where each esterification event occurred roughly twice as frequently as water addition. Consequently, the 4 to 6 ratio for aspartic acid (g) was 1:1 due to the requirement of two esterification events to produce the product, each contributing ½ an equivalent of 6g. This data indicates that diazofluorene produces a diazonium-carboxylate salt that is tightly held together by Coulombic forces in its solvent cage.[22] This allows for efficient reactivity, even in the presence of water as a competing nucleophile. An additional enhancement in selectivity was achieved with mercaptopropanoic acid. This is likely a result of coordination between the pendant thiol functionality and the intermediate diazonium ion, hindering external attack from water.

Carrying out the reaction in a 1:1 mixture of acetonitrile and MES-buffer resulted in a complete loss of selectivity with 1 while only a minor loss was observed for 2. Therefore, the electronics of the diazo compound plays an important role in determining its biological utility.

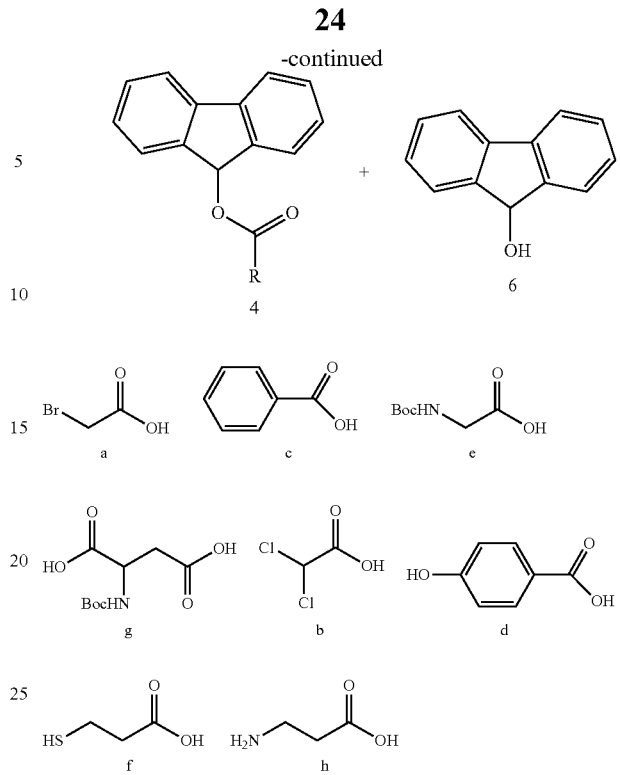

|  | Acid | | | | | | | | | | | | | | | |
|---|---|---|---|---|---|---|---|---|---|---|---|---|---|---|---|---|
|  | a | | b | | c | | d | | e | | f | | g | | h | |
| Diazo | 1 | 2 | 1 | 2 | 1 | 2 | 1 | 2 | 1 | 2 | 1 | 2 | 1 | 2 | 1 | 2 |
| 3:1 Acetonitrile:MES Buffer (pH = 5.5) | | | | | | | | | | | | | | | | |
| Ester | 1 | 2.0 | 1 | 2.7 | 1 | 2.3 | 1 | 2.0 | 1 | 2.3 | 1 | 6.7 | 1 | 1.0 | N/R | N/R |
| Alcohol | 4.2 | 1 | 4.6 | 1 | 3.9 | 1 | 1.8 | 1 | 12.9 | 1 | 3.6 | 1 | 4.9 | 1 | | |
| 1:1 Acetonitrile:MES Buffer (pH = 5.5) | | | | | | | | | | | | | | | | |
| Ester | 1 | 1.1 | 1 | 1.5 | 1 | 2.0 | 1 | 2.0 | 1 | 1.4 | 1 | 3.0 | 1 | 1 | N/R | N/R |
| Alcohol | 20 | 1 | 20 | 1 | 20 | 1 | 20 | 1 | 20 | 1 | 20 | 1 | 20 | 1.3 | | |

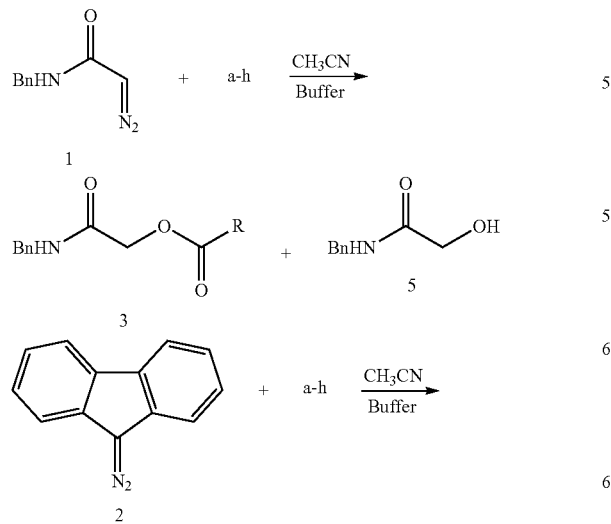

Scheme 2

A. Representative Procedure: Each Reaction was Reacted for 6 Hours and was Analyzed at that Time.

Diazofluorene (0.0060 g, 0.0313 mmol) was added to a solution of bromoacetic acid (0.0044 g, 0.0313 mmol) in a mixture of acetonitrile:MES buffer (10 mM, pH=5.5) (0.4 mL) and the reaction was allowed to stir 6 hours at room temperature. The reaction was concentrated and the ratio of products was determined by $^1$H-NMR. The ester data was reported above for each compound and below are the data for the hydrolysis products used for comparison.

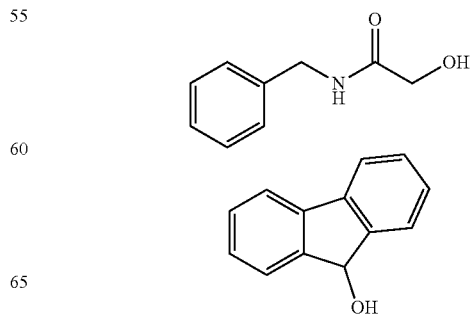

N-Benzylacetamidyl Hydrolysis Product (Left):

$^1$H NMR (400 MHz, CDCl$_3$) δ 7.38-7.28 (m, 5H), 4.52 (d, J=5.9 Hz, 2H), 4.19 (d, J=5.2 Hz, 2H), 2.24 (t, J=5.2 Hz, 1H). $^{13}$C NMR (126 MHz, CDCl$_3$) δ 171.2, 138.0, 129.0, 128.1, 127.9, 62.5, 43.3. HRMS (ESI) m/z 166.0864 [calc'd for C$_9$H$_{12}$NO$_2$ (M+H$^+$) 166.0863].

Fluorenyl Hydrolysis Product (Right):

$^1$H NMR (400 MHz, CDCl$_3$) 57.66 (d, J=7.6 Hz, 4H), 7.40 (t, J=7.6 Hz, 2H), 7.33 (t, J=7.6 Hz, 2H), 5.60 (bs, 1H). $^{13}$C NMR (126 MHz, CDCl$_3$) δ 145.8, 140.2, 129.3, 128.1, 125.4, 120.2, 75.5. HRMS (EI) m/z 182.0724 [calc'd for C$_{13}$H$_{10}$O (M$^+$) 182.0727].

Example 3: Thioester Vs. Thionoester Formation with Thioacetic Acid

Another useful probe for mechanistic insight in the comparison of the reaction of diazo compounds with thioacetic acid. It may be possible to observe different ratios of thio- vs. thionoester products depending on the rates of protonation and the subsequent nucleophilic attack. Reactivity was initially compared in anhydrous acetonitrile (Scheme 3). Complete selectivity for thioester was obtained with fluorenyl diazo compound 2. This selectivity rules out a cyclic transition state reminiscent of an ene reaction [25,26] which would predict the thionoester as the product. The greater basicity and therefore higher reactivity of diazoacetamide 1 on the other hand results in a mixture of products. The analogous reactions were also performed in the presence of buffer and showed complete thioester selectivity again with fluorenyl diazo compound 2, however, diazo acetamide 1 gave thioester and alcohol products with no trace of thionoester. The lack of thionoester formation in buffer can be attributed to the differential hydrogen bonding capabilities of sulfur and oxygen [27], greatly decreasing oxygen nucleophilicity relative to sulfur.

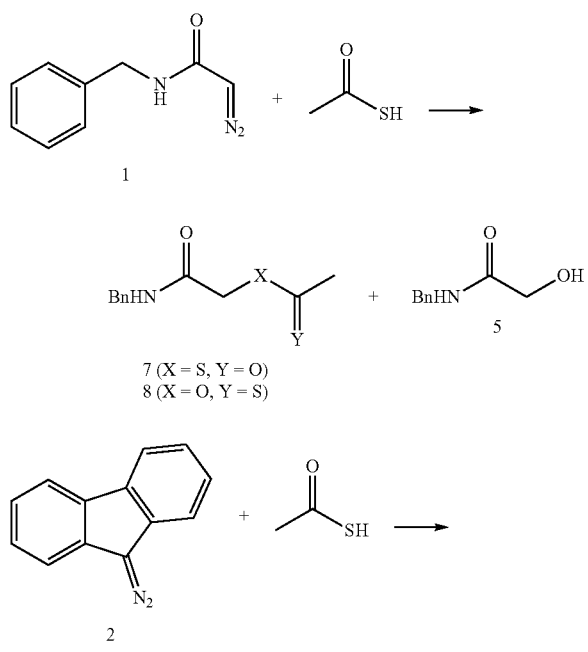

Scheme 3

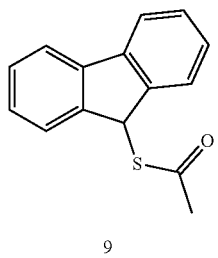

9

| Diazo | CH$_3$CN | CH$_3$CN: Buffer (3:1) |
|---|---|---|
| 1 | 7 (66%)$^a$<br>8 (66%) | 7 (84%)$^a$<br>5 (16%) |
| 2 | 9 (100%) | 7 (100%) |

$^a$Relative NMR yields

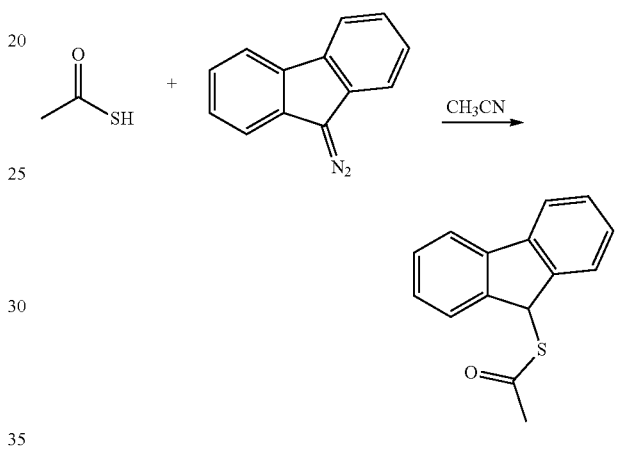

Diazofluorene (0.017 g, 0.089 mmol) was added to a solution of thioacetic acid (0.007 g, 0.089 mmol) in anhydrous acetonitrile (0.9 mL) and the reaction was allowed to stir 1 minute at room temperature until determined to be complete by thin-layer chromatography (R$_f$=0.8 in 30% EtOAc, 70% hexanes). The reaction was concentrated and purified by silica gel chromatography to give fluorenyl-thioacetate (0.020 g, 94%) in which sulfur was exclusively incorporated.

$^1$H NMR (400 MHz, CDCl$_3$) δ 7.73 (d, J=7.5 Hz, 2H), 7.54 (d, J=7.5 Hz, 2H), 7.40 (t, J=7.5 Hz, 2H), 7.32 (t, J=7.5 Hz, 2H), 5.88 (s, 1H), 2.52 (s, 3H). $^{13}$C NMR (126 MHz, CDCl$_3$) δ 196.3, 144.0, 140.9, 128.5, 127.8, 125.6, 120.2, 46.9, 30.7. HRMS (ESI) m/z 258.0953 [calc'd for C$_{15}$H$_{16}$NOS (M+NH$_4^+$) 258.0948].

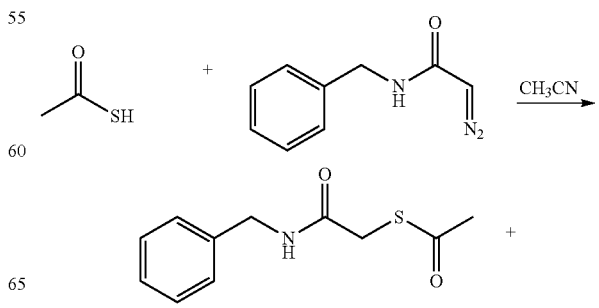

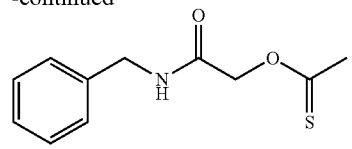

Diazobenzylacetamide (0.010 g, 0.057 mmol) was added to a solution of thioacetic acid (0.004 mL, 0.057 mmol) in anhydrous acetonitrile (0.57 mL) and the reaction was allowed to stir 1 hour at room temperature until determined to be complete by thin-layer chromatography ($R_f$=0.6, 0.7 in 70% EtOAc, 30% hexanes). The reaction was concentrated and purified by silica gel chromatography to give both benzyl acetamide-thioacetate (0.008 g, 62%) and benzyl-acetamido-thionoacetate (0.004 g, 31%).

Sulfur Attack (Benzyl-acetamide-thioacetate [Rf=0.6]):
$^1$H NMR (400 MHz, CDCl$_3$) δ 7.40-7.17 (m, 5H), 6.47 (bs, 1H), 4.43 (d, J=5.8 Hz, 2H), 3.59 (s, 2H), 2.39 (s, 3H). $^{13}$C NMR (126 MHz, CDCl$_3$) δ 195.9, 168.0, 137.8, 128.8, 127.6, 127.6, 43.8, 33.0, 30.3. HRMS (ESI) m/z 224.0746 [calc'd for C$_{11}$H$_{14}$NO$_2$S (M+H+) 224.0740].

Oxygen Attack (Benzyl-acetamide-thionoacetate [Rf=0.7]):
$^1$H NMR (400 MHz, CDCl$_3$) δ 7.44-7.25 (m, 5H), 6.39 (bs, 1H), 4.98 (s, 2H), 4.54 (d, J=5.9 Hz, 2H), 2.64 (s, 3H). $^{13}$C NMR (126 MHz, CDCl$_3$) δ 217.5, 166.1, 137.5, 128.9, 127.9, 127.8, 69.8, 43.2, 34.2. HRMS (ESI) m/z 246.0552 [calc'd for C$_{11}$H$_{13}$NO$_2$SNa (M+Na$^+$) 246.0560].

Example 4: RNase a Labeling Experiments and Esterase Cleavage Reactions

To address biocompatibility of diazo-compounds for esterification more directly, the relative esterification efficiency of these diazo compounds was compared with the eleven carboxyl groups present in ribonuclease A (RNase A). [24] In aqueous solvent mixtures, fluorenyl diazo 2 displays higher esterification efficiency than diazoacetamide 1; this presages a higher degree of labelling of RNase A.

In reactivity screens using 10 equivalents of diazo compound for 4 hours at 37° C., diazo-fluorene 2 esterified an average of three of the eleven carboxylates, while diazo-acetamide 1 proved incapable of labelling under these conditions. Only after the addition of 200 equivalents was any esterification with diazo-acetamide 1 observed which correlates with its lack of selectivity under aqueous conditions (Scheme 2).

Using trypsin digestion coupled with mass spectrometry, it was determined which residues were labelled and the results fit well with the observed chemoselectivity of each diazo compound. Diazofluorene 2, which labels an average of 3 residues (10 equiv.), displayed high chemoselectivity by almost exclusively labelling Asp14, Glu49, Glu111, and Asp121. Diazoacetamide 1, which labels an average of <1 residue (200 equiv.), was shown to be completely non-selective by comparably labelling residues Glu9, Asp14, Glu49, Glu111, and the C-terminal Val124. This provides further evidence that properly tuned diazo compounds can not only attain high levels of labelling, but can also selectively label specific residues. Prolonged treatment of the labelled RNaseA samples with esterase from *Saccharomyces cerevisiae* resulted in the regeneration of native protein (MALDI-MS). Thus, the esters formed employing the diazo-compounds were found to be bioreversible.

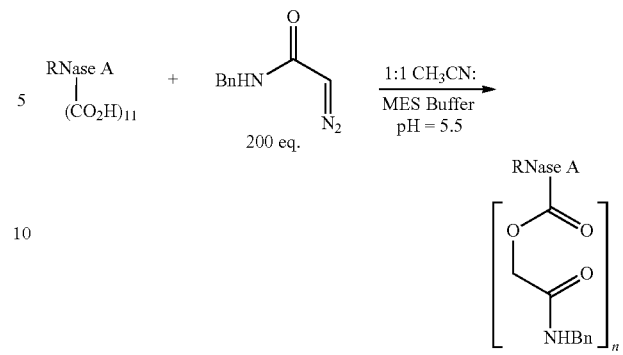

Ribonuclease A (0.001 g, 0.073 μmol) was dissolved in MES buffer (10 mM, pH=5.5, 0.1 mL) and diazobenzylac-etamide (0.0026 g, 14.6 μmol) was dissolved in acetonitrile (0.1 mL). The two solutions were combined and the reaction was allowed to stir 4 hours at 37° C. Any remaining diazo compound was then quenched by adding 0.1 M acetic acid (0.1 mL) and the reaction was concentrated and the extent of labeling was determined by MALDI spectroscopy to be <1 label per RNase A. (Note: When the same conditions were employed with only 10 equivalents of diazo compound, no labeling was observed).

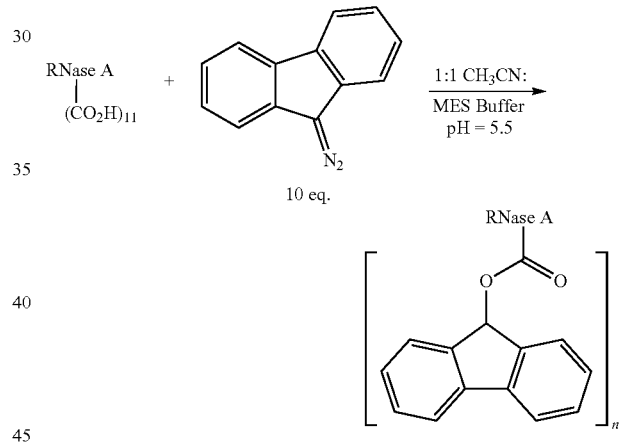

Ribonuclease A (0.001 g, 0.073 μmol) was dissolved in MES buffer (10 mM, pH=5.5, 0.1 mL) and a stock solution of diazofluorene in acetonitrile was made (Stock solution: 0.001 g, 7.30 μmol, 1 mL CH$_3$CN). The stock solution of diazo compound (0.1 mL, 0.730 μmol) was added to the ribonuclease solution and the reaction was allowed to stir 4 hours at 37° C. Any remaining diazo compound was then quenched by adding 0.1 M acetic acid (0.1 mL) and the reaction was concentrated and the extent of labeling was determined by MALDI spectroscopy to be 3 labels per RNase A.

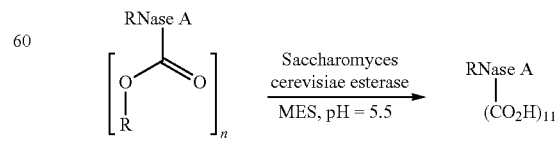

Each respective labeled sample of RNase A (0.001 g, 0.073 μmol) was dissolved in MES buffer (10 mM, pH=5.5, 0.2 mL) and treated with *Saccharomyces cerevisiae* esterase (0.001 g) for 24 h at 37° C. The reactions were then analyzed by MALDI-MS to confirm the regeneration of unlabeled RNase A.

REFERENCES (1) Trost, B. M. Science 1983, 219, 245.
(2) Trost, B. M.; Salzmann, T. N. J. Am. Chem. Soc. 1973, 95, 6840.
(3) Yamamoto, Y.; Toi, H.; Sonoda, A.; Murahashi, S. I. J. Am. chem. Soc. 1976, 98, 1965.
(4) McGrath, N. A.; Raines, R. T. Chem. Sci. 2012, 3, 3237.
(5) Myers, E. L.; Raines, R. T. Angew. Chem. Int. Ed. 2009, 48, 2359.
(6) Chibnall, A. C.; Mangan, J. L.; Rees, M. W. Biochem. J. 1958, 68, 114.
(7) Tian, L.; Yang, Y.; Wysocki, L. M.; Arnold, A. C.; Hu, A.; Ravichandran, B.; Sternson, S. M.; Looger, L. L.; Lavis, L. D. P Natl. Acad. Sci. USA 2012, 109, 4756.
(8) Boyce, M.; Bertozzi, C. R. Nat Methods 2011, 8, 638.
(9) Ye, T.; McKervey, M. A. Chem. Rev. 1994, 94, 1091.
(10) Doyle, M. P. Chem. Rev. 1986, 86, 919.
(11) Bertelsen, S.; Nielsen, M.; Bachmann, S.; Jorgensen, K. A. Synthesis-Stuttgart 2005, 2234.
(12) Shinada, T.; Kawakami, T.; Sakai, H.; Takada, I.; Ohfune, Y. Tetrahedron Lett. 1998, 39, 3757.
(13) Dumitrescu, L.; Azzouzi-Zriba, K.; Bonnet-Delpon, D.; Crousse, B. Org. Lett. 2011, 13, 692.
(14) De, K.; Legros, J.; Crousse, B.; Bonnet-Delpon, D. J. Org. Chem. 2009, 74, 6260.
(15) Furrow, M. E.; Myers, A. G. J. Am. Chem. Soc. 2004, 126, 12222.
(16) Riehm, J. P.; Scheraga, H. A. Biochemistry 1965, 4, 772.
(17) Delpierre, G. R.; Fruton, J. S. P Natl. Acad. Sci. USA 1965, 54, 1161.
(18) Doscher, M. S.; Wilcox, P. E. J. Biol. Chem. 1961, 236, 1328.
(19) Grossberg, A. L.; Pressman, D. J. Am. Chem. Soc. 1960, 82, 5478.
(20) Láznícek, M.; Lázníčková, A. J. Pharmaceut. Biomed. 1995, 13, 823.
(21) McGarrity, J. F.; Smyth, T. J. Am. Chem. Soc. 1980, 102, 7303.
(22) Szele, I.; Tencer, M.; Zollinger, H. Helv. Chim. Acta 1983, 66, 1691.
(23) Larson, J. R.; Epiotis, N. D. J. Am. Chem. Soc. 1981, 103, 410.
(24) Raines, R. T. Chem. Rev. 1998, 98, 1045.
(25) Alder, K.; Pascher, F.; Schmitz, A. Ber. Dtsch. Chem. Ges. 1943, 76, 27.
(26) Bachrach, S. M.; Jiang, S. L. J. Org. Chem. 1997, 62, 8319.
(27) Zhou, P.; Tian, F. F.; Lv, F. L.; Shang, Z. C. Proteins 2009, 76, 151.
(28) F. G. Bordwell (1988) Acc. Chem. Res. 21, 456, 463. A Table of pKa data of acidity of various organic compounds in DMSO is found at http://www.chem.wisc.edu/areas/reich/pkatable/
(29) F. G. Bordwell et al. J. Am. Chem. Soc. 1975, 97, 7006.
(30) F. G. Bordwell et al. J. Org. Chem. 1980, 45, 3325.
(31) F. G. Bordwell et al. J. Org. Chem. 1981, 46, 632.
(32) F. G. Bordwell et al. J. Am. Chem. Soc. 1983, 105, 6188.
(33) F. G. Bordwell et al. J. Org. Chem. 1990, 55, 3330.
(34) F. G. Bordwell et al. J. Org. Chem. 1991, 56, 4218.
(35) F. G. Bordwell et al. Can. J. Chem. 1990, 68, 1714.

The invention claimed is:

1. A method for esterification of one or more carboxylic acid groups in a compound containing one or more carboxylic acid groups which comprises the step of reacting the one or more carboxylic acids groups of the compound with a diazo-compound of formula:

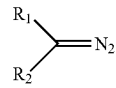

wherein the $R_1$ and $R_2$ groups of the diazo compound are selected such that the corresponding organic compound of formula:

exhibits a —C—H pKa value between 18 and 29 as measured in DMSO, wherein the one or more esters formed are bio-reversible, wherein the reaction is carried out in buffered aqueous solvent at a pH between 5 and 7, in the absence of catalyst, and wherein the compound containing the one or more carboxylic acid groups is not an amino acid.

2. The method of claim 1, wherein:
$R_1$ is hydrogen, or an optionally substituted alkyl, alkenyl, alkynyl, aryl, alkyl aryl, aryl alkyl, heteroaryl, or heterocyclic group;
$R_2$ is an optionally substituted alkyl, alkenyl, alkynyl, aryl, alkyl aryl, aryl alkyl, heteroaryl, heterocyclic group, where optionally $R_1$ and $R_2$ together form a 5- to 10-member ring which may be an optionally substituted carbocyclic ring or an optionally substituted heterocyclic ring in which one or more of the ring atoms can be replaced with —CO—, —O—, —CS—, —S— or —NR—, where R is hydrogen or an alkyl having 1-3 carbon atoms.

3. The method of claim 1, wherein at least one of $R_1$ or $R_2$ comprises an electron withdrawing group (EWG) or $R_1$ or $R_2$ together form a 5- to 10-member ring which comprises or is substituted with one or more EWG.

4. The method of claim 1, wherein one or both of $R_1$ or $R_2$ are alkyl, alkenyl, alkynyl, aryl, alkyl aryl, aryl alkyl groups substituted with one or more EWG.

5. The method of claim 2, wherein the EWG is selected from nitro, cyano, halogen, —NR'$_3^+$—, aryloxy, alkoxy, —SO$_2$—R', —S(R')$_2^+$, —P(R')$_3^+$, —COOR', —COR', —CON(R')$_2$, —OCOR', alkylthio, arylthio, aryl, —C≡CR', and —C═CR'$_2$, where each R', independently, is hydrogen, or an optionally substituted alky, alkenyl, alkynyl, aryl, alkylaryl, or arylalkyl, where two R' on the same atom may together with that atom form a 5- to 8-member carbocyclic or heterocyclic ring in which one or more ring atoms are optionally replaced with —CO—, —O—, —CS—, —S— or —NR—, where R is hydrogen or an alkyl group having 1-3 carbon atoms.

6. The method of claim 1, wherein the reaction is carried out in aqueous acetonitrile.

7. The method of claim 1, wherein the compound to be esterified contains one or more amino groups, hydroxyl groups or thiol groups in addition to the one or more carboxylic acid groups.

8. The method of claim 1, where the compound containing one or more carboxylic acid groups is a protein.

9. The method of claim 2, where the compound containing one or more carboxylic acid groups is a protein.

10. The method of claim 1, wherein the diazo-compound is a compound of formula II, III or IIIA:

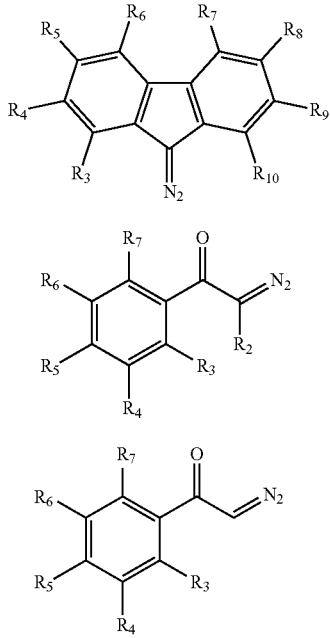

where:
- $R_2$ is selected from hydrogen, alkyl, alkenyl, alkynyl, alkoxy, aryl, aryloxy, carbocyclic, carbocyclyloxy, heteroaryl, heteroaryloxy, heterocyclyl, or heterocyclyloxy, each of which groups is optionally substituted;
- $R_3$-$R_{10}$ are selected from hydrogen, alkyl, alkoxy, alkenyl, alkenoxy, alkynyl, alkynoxy, aryl, aryloxy, alkylaryl, alkylaryloxy, arylalkyl, arylalkyloxy, heteroaryl, heteroaryloxy, carbocyclic, carbocyclyloxy, heterocyclic and heterocyclyloxy group, each of which is optionally substituted; or
- $R_3$-$R_{10}$ are selected from non-hydrogen substituents selected from the group consisting of halogen, hydroxyl, nitro, cyano, isocyano, thiocyano, isothiocyano, sulfuryl, —N(R')$_2$, —COR', —COOR', —CON(R')$_2$, —NR'—CO—R', —NR'—CO—N(R')$_2$—, —CO—SR', —SO$_2$—NR'$_2$, —OR', and —SR', where each R', independently, is selected from hydrogen, alkyl, alkenyl, alkynyl, aryl, heteroaryl, heterocyclic groups, each of which groups is optionally substituted; or
- two of $R_3$-$R_{10}$ are linked together to form an optionally substituted carbocyclic, aryl, heterocyclic or heteroaryl ring, wherein one or two carbons of the ring are optionally replaced with —CO— and the carbocyclic or heterocyclic rings are saturated or unsaturated.

11. The method of claim 1, wherein the diazo-compound is diazofluorene.

12. The method of claim 1, wherein the diazo-compound is a compound of formula:

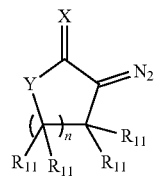

where:
- X is —O— or —S—, Y is —O—, —S— or —NR"—, where R" is hydrogen or an alkyl group;
- n is 1-5; and
- each $R_{11}$ is independently hydrogen, optionally substituted alkyl, optionally substituted carbocyclic, optionally substituted heterocyclic, —N(R')$_2$, —COR', —COOR', —CON(R')$_2$, —NR'—CO—R', —NR'—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, and heterocyclic groups, each of which groups is optionally substituted; or
- two or three $R_{11}$ together form a 3-8 member carbocyclic or heterocyclic ring in which one or two carbons are optionally replaced with —CO— and which rings are saturated or unsaturated.

13. The method of claim 1, wherein the diazo-compound is a compound of formula:

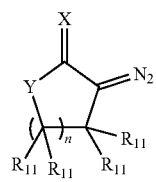

where:
- X is —O—, Y is —O—, n is 1 or 2; and
- each $R_{11}$ is independently hydrogen, optionally substituted alkyl, optionally substituted carbocyclic, optionally substituted heterocyclic, —N(R')$_2$, —COR', —COOR', —CON(R')$_2$, —NR'—CO—R', —NR'—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, and heterocyclic groups, each of which groups is optionally substituted; or
- two or three $R_{11}$ together form a 3-8 member carbocyclic or heterocyclic ring in which one or two carbons are optionally replaced with —CO— and which rings are saturated or unsaturated.

14. The method of claim 1, wherein the diazo-compound is a compound of formula:

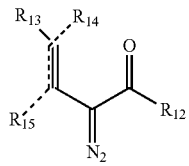

where:
- the dotted lines indicate that the bond is a double bond or a triple bond; if the bond is a double bond then $R_{14}$ and $R_{15}$ are present, if the bond is a triple bond $R_{14}$ and $R_{15}$ are absent; $R_{13}$-$R_{15}$ are independently selected from hydrogen, halogen, alkyl, alkenyl, alkynyl, alkoxy, aryl, aryloxy, carbocyclic, carbocyclyloxy, heteroaryl, heteroaryloxy, heterocyclyl, and heterocyclyloxy, each of which groups is optionally substituted; and $R_{12}$ is selected from hydrogen, alkyl, alkenyl, alkynyl, alkoxy, aryl, aryloxy, carbocyclic, carbocyclyloxy, heteroaryl, heteroaryloxy, heterocyclyl, and heterocyclyloxy, each of which groups is optionally substituted.

15. The method of claim 1, wherein the diazo-compound is a compound of formula:

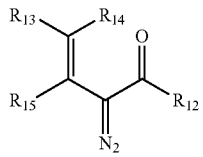

where:

$R_{13}$-$R_{15}$ are selected from hydrogen, halogen, alkyl, alkenyl, alkynyl, alkoxy, aryl, aryloxy, carbocyclic, carbocyclyloxy, heteroaryl, heteroaryloxy, heterocyclyl, and heterocyclyloxy, each of which groups is optionally substituted; and $R_{12}$ is selected from hydrogen, alkyl, alkenyl, alkynyl, alkoxy, aryl, aryloxy, carbocyclic, carbocyclyloxy, heteroaryl, heteroaryloxy, heterocyclyl, and heterocyclyloxy, each of which groups is optionally substituted.

16. The method of claim 1, wherein the diazo-compound is a compound of formula:

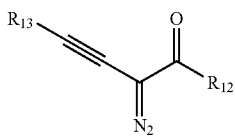

where:

$R_{13}$ is selected from hydrogen, halogen, alkyl, alkenyl, alkynyl, alkoxy, aryl, aryloxy, carbocyclic, carbocyclyloxy, heteroaryl, heteroaryloxy, heterocyclyl, or heterocyclyloxy, each of which groups is optionally substituted; and $R_{12}$ is selected from hydrogen, alkyl, alkenyl, alkynyl, alkoxy, aryl, aryloxy, carbocyclic, carbocyclyloxy, heteroaryl, heteroaryloxy, heterocyclyl, or heterocyclyloxy, each of which groups is optionally substituted.

17. The method of claim 1, wherein the diazo-compound is a compound of formula:

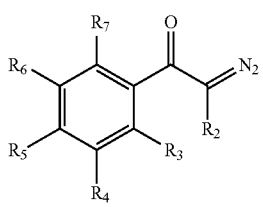

where:

$R_2$ is selected from hydrogen, alkyl, alkenyl, alkynyl, alkoxy, aryl, aryloxy, carbocyclic, carbocyclyloxy, heteroaryl, heteroaryloxy, heterocyclyl, and heterocyclyloxy, each of which groups is optionally substituted;

$R_3$-$R_7$ are independently selected from hydrogen, halogen, hydroxyl, nitro, cyano, isocyano, thiocyano, isothiocyano, sulfuryl, —N(R')$_2$, —COR', —COOR', —CON(R')$_2$, —NR'—CO—R', —NR'—CO—N(R')$_2$—, —CO—SR', —SO$_2$—NR'$_2$, —OR', —SR', alkyl, alkoxy, alkenyl, alkenoxy, alkynyl, alkynoxy, aryl, aryloxy, alkylaryl, alkylaryloxy, arylalkyl, arylalkyloxy, heteroaryl, heteroaryloxy, carbocyclic, carbocyclyloxy, heterocyclic or heterocyclyloxy group, each of which groups is optionally substituted, and where each R' is independently selected from hydrogen, alkyl, alkenyl, alkynyl, aryl, heteroaryl, and heterocyclic groups, each of which groups is optionally substituted.

18. The method of claim 1, for selective esterification of carboxylic acid groups in a protein in the presence of amine, hydroxyl or thiol groups therein.

19. The method of claim 18, wherein:

$R_1$ is hydrogen, or an optionally substituted alkyl, alkenyl, alkynyl, aryl, alkyl aryl, aryl alkyl, heteroaryl, or heterocyclic group;

$R_2$ is an optionally substituted alkyl, alkenyl, alkynyl, aryl, alkyl aryl, aryl alkyl, heteroaryl, or heterocyclic group, where optionally $R_1$ and $R_2$ together form a 5- to 10-member ring which is an optionally substituted carbocyclic ring or an optionally substituted heterocyclic ring in which one or more of the ring atoms can be replaced with —CO—, —O—, —CS—, —S— or —NR—, where R is hydrogen or an alkyl having 1-3 carbon atoms.

20. The method of claim 1, wherein a carboxylic acid groups in a side chain of the peptides or proteins are esterified.

21. The method of claim 1, wherein the reaction is carried out in buffered aqueous solvent at a pH between 5.5 and 6.5.

22. The method of claim 1, wherein the reaction is carried out in buffered aqueous solvent containing from 10-70% (by volume) of buffer.

23. The method of claim 1 for esterification of carboxylic acid groups in a protein, wherein the reaction is carried out in buffered aqueous acetonitrile containing from 10-70% (by volume) of buffer.

24. The method of claim 23, wherein the diazo compound is diazofluorene.

25. The method of claim 1, wherein the reacting step consists of reacting the one or more carboxylic acids groups of the compound with the diazo-compound.

* * * * *